US006893865B1

(12) United States Patent
Lockert et al.

(10) Patent No.: US 6,893,865 B1
(45) Date of Patent: May 17, 2005

(54) METHODS, COMPOSITIONS, AND CELLS FOR ENCAPSIDATING RECOMBINANT VECTORS IN AAV PARTICLES

(75) Inventors: Dara H. Lockert, Seattle, WA (US); Carmel M. Lynch, Kenmore, WA (US); Haim Burstein, Sammamish, WA (US); Anthony M. Stephan, Seattle, WA (US)

(73) Assignee: Targeted Genetics Corporation, Seattle, WA (US)

( * ) Notice: Subject to any disclaimer, the term of this patent is extended or adjusted under 35 U.S.C. 154(b) by 0 days.

(21) Appl. No.: 09/561,190

(22) Filed: Apr. 27, 2000

Related U.S. Application Data

(60) Provisional application No. 60/135,119, filed on Apr. 28, 1999.

(51) Int. Cl.[7] .................. C12N 15/80; C12N 15/83; C12N 15/86; C12N 15/87
(52) U.S. Cl. ............. 435/320.1; 435/91.1; 435/91.33; 435/91.4; 435/94.41; 435/91.42; 530/300; 514/24.1
(58) Field of Search .................. 435/320, 422, 435/91.1, 91.33, 91.4, 91.42; 425/186.1, 233.1; 536/24.3; 530/389.4

(56) References Cited

U.S. PATENT DOCUMENTS

| | | |
|---|---|---|
| 5,139,941 A | 8/1992 | Muzyczka et al. |
| 5,173,414 A | 12/1992 | Lebkowski et al. |
| 5,354,678 A | 10/1994 | Lebkowski et al. |
| 5,580,703 A | 12/1996 | Kotin et al. |
| 5,587,308 A | 12/1996 | Carter et al. |
| 5,652,224 A | 7/1997 | Wilson et al. |
| 5,658,776 A | 8/1997 | Flotte et al. |
| 5,658,785 A | 8/1997 | Johnson |
| 5,756,283 A | 5/1998 | Wilson et al. |
| 5,786,211 A | 7/1998 | Johnson |
| 5,837,484 A | 11/1998 | Trempe et al. |
| 5,843,742 A | 12/1998 | Natsoulis et al. |
| 5,846,528 A | 12/1998 | Podsakoff et al. |
| 5,856,152 A | 1/1999 | Wilson et al. |
| 5,858,351 A | 1/1999 | Podsakoff et al. |
| 5,858,775 A | 1/1999 | Johnson |
| 5,866,552 A | 2/1999 | Wilson et al. |
| 5,866,696 A | 2/1999 | Carter et al. |
| 5,869,305 A * | 2/1999 | Samulski et al. ........ 435/172.3 |
| 5,871,982 A | 2/1999 | Wilson et al. |
| 5,872,154 A | 2/1999 | Wilson et al. |
| 5,989,540 A | 11/1999 | Carter et al. |
| 5,990,279 A | 11/1999 | Carter et al. |
| 6,165,781 A | 12/2000 | Carter et al. |
| 6,174,527 B1 | 1/2001 | Wilson et al. |
| 6,211,160 B1 | 4/2001 | Wilson et al. |
| 6,251,677 B1 | 6/2001 | Wilson et al. |
| 6,251,957 B1 | 6/2001 | Wilson et al. |
| 6,258,595 B1 | 7/2001 | Gao et al. |
| 6,261,551 B1 | 7/2001 | Wilson et al. |
| 6,270,996 B1 | 8/2001 | Wilson et al. |
| 6,274,354 B1 | 8/2001 | Wilson et al. |
| 6,281,010 B1 | 8/2001 | Gao et al. |
| 6,346,415 B1 | 2/2002 | Feldhaus |
| 6,372,208 B1 | 4/2002 | Wilson et al. |
| 6,387,368 B1 | 5/2002 | Wilson et al. |
| 6,399,385 B1 | 6/2002 | Croyle et al. |
| 6,436,392 B1 | 8/2002 | Engelhardt et al. |
| 6,475,769 B1 | 11/2002 | Wilson et al. |
| 6,482,634 B1 | 11/2002 | Wilson et al. |
| 6,485,966 B2 | 11/2002 | Gao et al. |
| 6,537,540 B1 | 3/2003 | Burstein et al. |
| 6,541,258 B2 | 4/2003 | Allen et al. |
| 6,566,118 B1 | 5/2003 | Atkinson et al. |
| 6,596,535 B1 | 7/2003 | Carter |
| 6,642,051 B1 | 11/2003 | Lynch et al. |
| 6,759,237 B1 | 7/2004 | Wilson et al. |
| 2001/0006955 A1 | 7/2001 | Wilson et al. |
| 2002/0001581 A1 | 1/2002 | Lynch et al. |
| 2002/0037867 A1 | 3/2002 | Wilson et al. |
| 2002/0127582 A1 | 9/2002 | Atkinson et al. |
| 2002/0131956 A1 | 9/2002 | Walsh et al. |
| 2002/0160501 A1 | 10/2002 | Atkinson et al. |
| 2002/0164783 A1 | 11/2002 | Feldhaus |
| 2002/0182182 A1 | 12/2002 | Wilson et al. |
| 2002/0197237 A1 | 12/2002 | Engelhardt et al. |
| 2003/0040101 A1 | 2/2003 | Wilson et al. |
| 2003/0073232 A1 | 4/2003 | Wilson et al. |
| 2003/0082145 A1 | 5/2003 | Johnson |
| 2003/0103939 A1 | 6/2003 | Engelhardt et al. |
| 2003/0103942 A1 | 6/2003 | Burstein et al. |
| 2003/0113295 A1 | 6/2003 | Burstein et al. |
| 2003/0119191 A1 | 6/2003 | Gao et al. |

(Continued)

FOREIGN PATENT DOCUMENTS

| | | |
|---|---|---|
| EP | 0 488 528 | 6/1992 |
| WO | WO 92/08796 | 5/1992 |

(Continued)

OTHER PUBLICATIONS

Merriam Webster's Collegiate Dictionary Tehth Edition, p. 823 and 108.*

(Continued)

*Primary Examiner*—James Housel
*Assistant Examiner*—Bao Qun Li
(74) *Attorney, Agent, or Firm*—Morrison & Foerster

(57) ABSTRACT

Isolated recombinant polynucleotides comprising elements which promote encapsidation into AAV particles, packaging cells comprising the recombinant polynucleotides, and methods for their use are provided in the present invention. These isolated recombinant polynucleotides comprise a non-AAV ITR encapsidation element (such as the P1 sequence located within the AAV S1 integration site of human chromosome 19) operably linked to one or more heterologous genes to be encapsidated. The constructs may be either integrated into a mammalian cell genome, maintained episomally, or provided transiently.

18 Claims, 6 Drawing Sheets

U.S. PATENT DOCUMENTS

| | | |
|---|---|---|
| 2003/0175974 A1 | 9/2003 | Allen |
| 2003/0219735 A1 | 11/2003 | Carter |
| 2004/0052764 A1 | 3/2004 | Hildinger et al. |
| 2004/0057931 A1 | 3/2004 | Wilson et al. |
| 2004/0057932 A1 | 3/2004 | Wilson et al. |
| 2004/0057933 A1 | 3/2004 | Wilson et al. |
| 2004/0062752 A1 | 4/2004 | Walsh et al. |

FOREIGN PATENT DOCUMENTS

| | | |
|---|---|---|
| WO | WO 93/24641 | 12/1993 |
| WO | WO 94/13788 | 6/1994 |
| WO | WO 94/28143 | 12/1994 |
| WO | WO 95/06743 | 3/1995 |
| WO | WO 95/13365 | 5/1995 |
| WO | WO 95/13392 | 5/1995 |
| WO | WO 95/14771 | 6/1995 |
| WO | WO 95/20671 | 8/1995 |
| WO | WO 95/34670 | 12/1995 |
| WO | WO 96/00587 | 1/1996 |
| WO | WO 96/13598 | 5/1996 |
| WO | WO 96/17947 | 6/1996 |
| WO | WO 96/26285 | 8/1996 |
| WO | WO 96/26286 | 8/1996 |
| WO | WO 96/39530 | 12/1996 |
| WO | WO 97/09441 | 3/1997 |
| WO | WO 97/09442 * | 3/1997 |
| WO | WO 97/32990 | 9/1997 |
| WO | WO 98/09656 | 3/1998 |
| WO | WO 98/09657 | 3/1998 |
| WO | WO 98/10086 | 3/1998 |
| WO | WO 98/10088 | 3/1998 |
| WO | WO 98/27204 | 6/1998 |
| WO | WO 98/27207 | 6/1998 |
| WO | WO 99/11764 | 3/1999 |
| WO | WO 99/14351 | 3/1999 |
| WO | WO 99/15677 | 4/1999 |
| WO | WO 99/15685 | 4/1999 |
| WO | WO 99/20773 | 4/1999 |
| WO | WO 99/20779 | 4/1999 |
| WO | WO 99/47691 | 9/1999 |
| WO | WO 99/60146 | 11/1999 |
| WO | WO 00/14205 | 3/2000 |
| WO | WO 00/28061 | 5/2000 |
| WO | WO 00/53788 A2 | 9/2000 |
| WO | WO 00/55342 | 9/2000 |
| WO | WO 00/65038 | 11/2000 |
| WO | WO 00/73480 | 12/2000 |
| WO | WO 00/73481 | 12/2000 |
| WO | WO 00/75353 | 12/2000 |
| WO | WO 00/75365 | 12/2000 |
| WO | WO 01/11034 | 2/2001 |
| WO | WO 01/23001 | 4/2001 |
| WO | WO 01/25462 | 4/2001 |
| WO | WO 01/25465 | 4/2001 |
| WO | WO 01/27303 | 4/2001 |
| WO | WO 01/83692 | 11/2001 |
| WO | WO 01/83730 | 11/2001 |
| WO | WO 03/006616 | 1/2003 |
| WO | PCT/US2004/009950 | 3/2004 |
| WO | PCT/US2004/010045 | 3/2004 |

OTHER PUBLICATIONS

Chiorini et al. Human Gene Ther. 1995, vol. 6, pp. 1531–1541.*

Salvetti, A. et al. (1998) "Factors Influencing Recombinant Adeno–Associated Virus Production," *Human Gene Therapy* 9(5):695–706.

Zhou, X. and Muzyczka, N. (1998). "In Vitro Packaging of Adeno–Associated Virus DNA," *Journal of Virology* 72(4):3241–3247.

U.S. Appl. No. 09/578,561, Rasty et al., filed May 25, 2000.

U.S. Appl. No. 09/665,852, Wilson et al., filed Sep. 20, 2000.

U.S. Appl. No. 09/684,554, Engelhardt et al., filed Oct. 6, 2000.

U.S. Appl. No. 09/689,136, Engelhardt et al., filed Oct. 12, 2000.

U.S. Appl. No. 09/689,430, Walsh et al., filed Oct. 12, 2000.

U.S. Appl. No. 10/089,394, Chen et al., filed Mar. 29, 2002.

U.S. Appl. No. 10/375,777, Johnson, filed Feb. 26, 2003.

U.S. Appl. No. 10/615,119, Lynch et al., filed Jul. 7, 2003.

U.S. Appl. No. 10/815,262, Engelhardt et al., filed Mar. 31, 2004.

U.S. Appl. No. 10/815,557, Engelhardt et al., filed Mar. 31, 2004.

U.S. Appl. No. 10/837,029, Engelhardt et al., filed Apr. 30, 2004.

Flotte, T.R. et al. (1995). "An Improved System for Packaging Recombinant Adeno–Associated Virus Vectors Capable of In Vivo Transduction," *Gene Ther.* 2:29–37.

Giraud, C. et al. (1995). "Recombinant Junctions Formed by Site–Specific Integration of Adeno–Associated Virus into an Episome," *J. Virol.* 69(11):6917–6924.

Giraud, C. et al. (1994). "Site–Specific Integration by Adeno–Associated Virus is Directed by a Cellular DNA Sequence," *Proc. Natl. Acad. Sci. USA* 91:10039–10043.

Linden, R.M. et al. (1996). "Site–Specific Integration by Adeno–Associated Virus," *Proc. Natl. Acad. Sci. USA* 93:11288–11294.

Samulski, R.J. et al. (1989). "Helper–Free Stocks of Recombinant Adeno–Associated Viruses: Normal Integration does Not Require Viral Gene Expression," *J. Virol.* 63(9):3822–3828.

Srivastiva, C.H. et al. (1989). "Construction of a Recombinant Human Parvovirus B19: Adeno–Associated VIrus 2 (AAV) DNA Inverted Terminal Repeats are Functional in an AAV–B19 Hybrid Virus," *Proc. Natl. Acad. Sci. USA* 86:8078–8082.

Tratschin, J.–D. et al. (1984). "A Human Parvovirus, Adeno–Associated Virus, as a Eucaryotic Vector: Transient Expression and Encapsidation of the Procaryotic Gene for Chloramphenicol Acetyltransferase," *Mol. Cell. Biol.* 4(10):2072–2081.

Tratschin, J.–D. et al. (1985.) "Adeno–Associated Virus Vector for High–Frequency Integration, Expression, and Rescue of Genes in Mammalian Cells," *Moll. Cell. Biol.* 5(11):3251–3260.

Vincent, K.A. et al. (1990). "Replication and Packaging of HIV Envelope Genes in a Novel Adeno–Associated Virus Vector System" *Vaccines 90*, Cold Spring Harbor Laboratory Press: New York. Brown, F. et al. eds. pp. 353–359.

Afione, S.A. et al. (May 1996). "In Vivo Model of Adeno–Associated Virus Vector Persistence and Rescue," *J. Virol.* 70(5):3235–3241.

Anoymous "Blast 2.0 Release Notes" Web Page revised Dec. 18, 1998, at <http://www.ncbi.nlm.nih.gov/BLAST/newblast.html>, 18 pages.

Arispe, N. et al. (Mar. 1, 1992). "Intrinsic Anion Channel Activity of the Recombinant First Nucleotide Binding Fold Domain of the Cystic Fibrosis Transmembrane Regulator Protein," *Proc. Natl. Acad. Sci. USA* 89:1539–1543.

Balague, C. et al. (Apr. 1997). "Adeno–Associated Virus Rep78 Protein Terminal Repeats Enahnce Integration of DNA Sequences Into the Cellular Genome," *J. Virol.* 71(4):3299–3306.

Berns, K.I. (1990). "Chapter 62: Parvoviridae and Their Replication" *Virology*, Second Edition, edited by B.N. Fields, D.M. Knipe et al., Raven Press: New York. pp. 1743–1764.

Blacklow, N.I. (1988). "Chapter 11: Adeno–Associated Viruses of Humans" in *Parvoviruses and Human Disease*. Pattison J.R., Ed., CRC Press, Inc., Florida, pp. 165–174.

Boshart, M. et al. (Jun. 1985). "A Very Strong Enhancer is Located Upstream of an Immediate Early Gene of Human Cytomegalovirus," *Cell* 41(2):521–530.

Carter, B.J. et al. (1989). "Chapter 11: AAV DNA Replication, Integration, and Genetics" *CRC Handbook of Parvoviruses*. vol. 1, Tijssen, P. ed., CRC Press, Inc., Florida, pp. 169–228.

Carter, B.J. (Oct. 1992). "Adeno–Associated Virus Vectors," *Curr. Opin. Biotechnol.* 3(5):533–539.

Chejanovsky, N. et al. (Nov. 1989). "Mutagenesis of an AUG Codon in the Adeno–Associated Virus rep Gene: Effects on Viral DNA Replication," *Virology* 173(1):120–128.

Chiorini, J.A. et al. (Sep. 1997). "Cloning of Adeno–Associated Virus Type 4 (AAV4) and Generation of Recombinant AAV4 Particles," *J. Virol.* 71(9):6823–6833.

Chiorini, J.A. et al. (Mar 1999). "Adeno–Associated Virus (AAV) Type 5 Rep Protein Cleaves a Unique Terminal Resolution Site Compared With Other AAV Serotypes," *J. Virol.* 73(5):4293–4298.

Clowes, M.M. et al. (Feb. 1994). "Long–Term Biological Response of Injured Rat Carotid Artery Seeded With Smooth Muscle Cells Expressing Retrovirally Introduced Human Genes," *J. Clin. Invest.* 93(2):644–651.

Dong, J.–Y. et al. (Nov. 10, 1996). "Quantitative Analysis of the Packaging Capacity of Recombinanat Adeno0Associated Virus," *Human Gene Ther.* 7(17):2101–2112.

Egan, M. et al. (Aug. 13, 1992). "Defective Regulation of Outwardly Rectifying ClChannels by Protein Kinase A Corrected by Insertion of CFTR," *Nature* 358:581–584.

Flotte, T.R. et al. (Sep. 1992). "Gene Expression From Adeno–Associated Virus Vectors in Airway Epithelial Cells," *Am. J. Respir. Cell Mol. Biol.* 7(3):349–356.

Glotte, T.R. et al. (Feb. 1993). "Expression of he Cystic Fibrosis Transmembrane Conductance Regulator From a Novel Adeno–Associated Virus Promoter," *J. Biol. Chem.* 268(5):3781–3790.

Flotte, T.R. et al. (Nov. 1993). "Stable In Vivo Expression of the Cystic Fibrosis Transmembrane Conductance Regulator with an Adeno–Associated Virus Vector," *Proc. Natl. Acad. Sci. USA* 90:10613–10617.

Gottlieb, J. et al. (Jun. 1988). "In Vitro Excision of Adeno–Associated Virus DNA From Recombinanat Plasmids: Isolation of an Enzyme Fraction From HeLa Cells That Cleaves DNA at Poly(G) Sequences," *Mol. Cell. Biol.* 6(8):2513–2522.

Hermonat, P.L. et al. (Aug. 1984). "Genetics of Adeno–Associated Virus: Isolation and Preliminary Characterization of Adeno–Associated Virus Type 2 Mutants," *J. Virol.* 51(2):329–339.

Hölscher, C. et al. (Nov. 1994). "Cell Lines Inducibly Expressing the Adeno–Associated Virus (AAV) rep Gene: Requirements for Productive Replication of rep–Negative AAV Mutants," *J. Virol.* 68(11):7169–7177.

Hölscher, C. et al. (Nov. 1995). "High–Level Expression of Adeno Associated Virus (AAV) Rep78 or Rep68 Protein Is Sufficient for Infectious–Particle Formation by a rep–Negative AAV Mutant," *J. Virol.* 69(11):6880–6885.

Kelman, Z. and O'Donnell, M. (Apr. 1994). "DNA Replication: Enzymology and Mechanisms," *Curr. Opin. Genet. Dev.* 4(2):185–195.

Khleif, S.N. et al. (Apr. 1991). "Inhibition of Cellular Transformation by the Adeno–Associated Virus rep Gene," *Virology* 181:738–741.

Kotin, R.M. et al. (Dec. 1992). "Characterization of a Preferred Site on Human Chromosome 19q for Integration of Adeno–Associated Virus DNA by Non–Homologous Recombination," *EMBO J.* 11(13):5071–5078.

Labow, M.A. et al. (Apr. 1987). "Adeno–Associated Virus Gene Expression Inhibits Cellular Transformation by Heterologous Genes," *Mol. Cell. Biol.* 7(4):1320–1325.

Laughlin, C.A. et al. (Nov. 1979). "Spliced Adenovirus–Associated Virus RNA," *Proc. Natl. Acad. Sci. USA* 76(11):5567–5571.

Laughlin, C.A. et al. (Jul. 1983). "Cloning of Infectious Adeno–Associatd Virus Genomes in Bacterial Plasmids," *Genes* 23(1):65–73.

Lynch, C.M. et al. (Apr. 1997). "Adeno–Associated Virus Vectors for Vascular Gene Delivery," *Circ. Res.* 80(4):497–505.

Mendelson, E. et al. (Sep. 1988). "Expression and Rescue of a Nonselected Marker from an Integrated AAV Vector,", *Virology* 166(1):154–165.

Muramatsu, S.–I. et al. (Jul. 1, 1996). "Nucleotide Sequencing and Generation of an Infectious Clone of Adeno–Associated Virus 3," *Virology* 221(1):208–217.

Muzyczka, N. (1992). "Use of Adeno–Associated Virus as a General Transduction Vector for Mammalian Cells," *Curr. Topics. Microbiol. Immunol.* 158:97–129.

Rich, D.P. et al. (Jul. 12, 1991). "Effect of Delecting the R Domain on CFTR–Generated Chloride Channels," *Science* 253:205–207.

Rose, J.A. (1974). "Chapter 1. Parvovirus Reproduction" in *Comprehensive Virology*. Vol. 3, Plenum Press, New York, pp. 1–61.

Rutledge, E.A. et al. (Jan. 1998). "Infectious Clones and Vectors Derived from Adeno–Associated Virus (AAV) Serotypes Other Than AAV Type 2," *J. Virol.* 72(1):309–319.

Samulski, R.J. et al. (Mar. 1982). "Cloning of Adeno–Associated Virus Into pBR322: Rescue of Intact Virus From the Recombinant Plasmid in Human Cells," *Proc. Natl. Acad. Sci. USA* 79(6):2077–2081.

Samulski, R.J. et al. (May 1983). "Rescue of Adeno–Associated Virus From Recombinanat Plasmids: Gene Correction Within the Terminal Repeats of AAV," *Cell* 33(1):135–143.

Samulski, R.J. et al. (Oct. 1987). "A Recombinanat Plasmid From Which an Infectious Adeno–Associated Virus Genome can be Excised in Vitro and its Use to Study Viral Replication," *J. Virol.* 61(10):3096–3101.

Senapathy, P. and Carter, B.J. (Apr. 10, 1984). "Molecular Cloning of Adeno–Associated Virus Variant Genomes and Generation of Infectious Virus by Recombination in Mammalian Cells," *J. Biol. Chem.* 259(7):4661–4666.

Senapathy, P. et al. (Oct. 15, 1984). "Replication of Adeno–Associated Virus DNA. Complementation of Naturally Occurring rep Mutants by a Wild–Type Genome or an ori Mutant and Correction of Terminal Palindrome Deletions," *J. Mol. Biol.* 178,179:1–20.

Sheppard, D.N. et al. (Mar. 25, 1994). "The Amino–Terminal Portion of CFTR Forms a Regulated Cl$^-$Channel," *Cell* 76:1091–1098.

Simonsen, C.C. and Levinson A.D. (May 1983). "Isolation and Expression of an Altered Mouse Dihydrofolate Reductase cDNA," *Proc. Natl. Acad. Sci. USA* 80(9):2495–2499.

Srivastiva, A. et al. (Feb. 1983). "Nucleotide Sequence and Organization of the Adeno–Associated Virus 2 Genome," *J. Virol.* 45(2):555–564.

Tratschin, J.D. et al. (Sep. 1984). "Genetic Analysis of Adeno–Associated Virus: Properties of Deletion Mutants Constructed In Vitro and Evidence for an Adeno–Associated Virus Replication Function," *J. Virol.* 51(3):611–619.

Tratschin, J.D. et al. (Aug. 1986). "Negative and Positive Regulation in Trans of Gene Expression From Adeno–Associated Virus Vectors in Mammalina Cells by a Viral rep Gene Product," *Mol. Cell. Biol.* 6(8):2884–2894.

Urcelay, E. et al. (Apr. 1995). "Asymmetric Replication In Vitro From a Human Sequence Element is Dependent on Adeno–Associated Virus Rep Protein," *J. Virol.* 69(4):2038–2046.

Walsh, C.E. et al. (Aug. 1, 1992). "Regulated High Level Expression of a Human Gamma–Globin Gene Introduced Into Erythroid Cells by an Adeno–Associated Virus Vector," *Proc. Natl. Acad. Sci. USA* 89:7257–7261.

Wang, X.-S. et al. (1995). "Rescue and Replication Signals of the Adeno–Associated Virus 2 Genome," *J. Mol. Biol.* 250:573–580.

Wang, X.-S. et al. (Mar. 1996). "Rescue and Replication of Adeno–Associated Virus Type 2 as Well as Vector DNA Sequences Drom Recombinant Plasmids Containing Deletions in the Viral Inverted Terminal Repeats: Selective Encapsidation of Viral Genomes in Progeny Virions," *J. Virol.* 70(3):1668–1677.

Wang, X.-S. and Srivastava, A. (Feb. 1997). "A Novel Terminal Resolution–Like Site in the Adeno–Associated Virus Type 2 Genome," *J. Virol.* 71(2):1140–1146.

Wang, X.-S. et al. (Apr. 1997). "Adeno–Associated Virus Type 2 DNA Replication In Vivo: Mutation Analyses of the D Sequence in Viral Inverted Terminal Repeats," *J. Virol.* 71(4):3077–3082.

Weitzman, M.D. et al. (Jun. 1994). "Adeno–Associated Virus (AAV) Rep Proteins Mediate Complex Formation Between AAV DNA and its Integration Site in Human DNA," *Proc. Natl. Acad. Sci. USA* 91:5808–5812.

Wonderling, R.S. and Owens, R.A. (Mar. 1997). "Binding Sites for Adeno–Associated Virus Rep Proteins Within the Human Genome," *J. Virol.* 71(3):2528–2534.

Xiao, X. et al. (Feb. 1997). "A Nolvel 165–Base–Pair Terminal Repeat Sequences is the Sole cis Requirements for the Adeno–Associated Virus LIfe Cycle," *J. Virol.* 71(2):941–948.

Xiao, W. et al. (May 1999). "Gene Therapy Vectors Based on Adeno–Associated Virus Type 1," *J. Virol.* 73(5):3994–4003.

* cited by examiner

CCCGGGGCGGGCGGGCGGGCGGGTGGTGGCGGCGGTTGGGGCTCGGCGCTCGCTCGCTCGCTGGGCGGG
C

GGGCGGTGCGATGTCCGGAGAGGATGGCCGGCGGCTGGCCCGGG

FIGURE 1

P1
5'   CGGGCGGGTGGTGGCGGCGGTTGGGGCTCGGC-----GCTCGCTCGCTCGCTGGGCGGGCGGGCGGT
     ||         |  |  |||||             |   || ||||||||||||    |  |  ||
5'   AGGAACCCCTAGTGATGGAGTTGGCCACTCCCTCTCTGCGCGCTCGCTCGCTCACTGAGGCCGCCCC
     145                                                                79
AAV2 ITR

FIGURE 2

```
P1
5'   CGGGCGGGTGGTGGCGGCGGTTGGGGCTCGGC-----
GCTCGCTCGCTCGCTGGGCGGGCGGGCGGT
                |   |  ||||       |       || ||||||||||| || |||
5'      TTACCCCTAGTGATGGAGTTGCCCACTCCCTCTCTGCGCGCTCGCTCGCTCGGTGGGGC
AAV1 ITR

P1
5'   CGGGCGGGTGGTGGCGGCGGTTGGGGCTCGGC-----
GCTCGCTCGCTCGCTGGGCGGGCGGGCGGT
        |          |  |  ||||||    |      ||| | |||||||||| || |||
5'  GCCATACCTCTAGTGATGGAGTTGGCCACTCCCTCTATGCGCACTCGCTCGCTCGGTGGGGC
AAV3 ITR

P1
5'    CGGGCGGGTGGTGGCGGCGGTTGGGGCTCGGC---------GCTCGCTCGCTCGCTGGGCGGGCGGGCGGT
            |     | | |  |  |||||      |            ||||||||| ||| |||||||
5'  GGGCAAACCTAGATGATGAGTTGGCCACTCCCTCTATGCGCGCTCGCTCACTCACTCGGCC
AAV4 ITR

P1
5'    CGGGCGGGTGGTGGCGGCGGTTGGGGCTCGGC----------
GCTCGCTCGCTCGCTGGGCGGGCGGGCGGT
              |   | |     | |  |||  |||  |          | ||||||||||||||||  |   ||
||
5'
ACAAAACCTCCTTGCTTGAGAGTGTGGCACTCTCCCCCCTGTCGCGTTCGCTCGCTCGCTGGCTCGTTTGGGGGGG
AAV5 ITR

P1
5'    CGGGCGGGTGGTGGCGGCGGTTGGGGCTCGGC------GCTCGCTCGCTCGCTGGGCGGGCGGGCGGT
              | | |  |||   | |       || |||||||||||    | |
5'      TTACCCCTAGTGATGGAGTTGCCCACTCCCTCTCTGCGCGCTCGCTCGCTCACTGAGGCC
AAV6 ITR
```

FIGURE 3

METHODS, COMPOSITIONS, AND CELLS FOR ENCAPSIDATING RECOMBINANT VECTORS IN AAV PARTICLES

CROSS-REFERENCE TO RELATED APPLICATIONS

This application claims priority to U.S. provisional application 60/135,119 (converted from U.S. Ser. No. 09/301,514), filed Apr. 28, 1999, which is incorporated by reference in its entirety.

STATEMENT OF RIGHTS TO INVENTIONS MADE UNDER FEDERALLY SPONSORED RESEARCH (Not applicable)

TECHNICAL FIELD

This invention is in the field of recombinant DNA constructs for gene delivery. More specifically, the invention is in the field of recombinant DNA constructs for use in the production of recombinant DNA vectors for gene delivery.

BACKGROUND ART

Vectors based on adeno-associated virus (AAV) are believed to have utility for gene therapy but a significant obstacle has been the difficulty in generating such vectors in amounts that would be clinically useful for human gene therapy applications. This is a particular problem for in vivo applications such as direct delivery to the lung. Another important goal in the gene therapy context, discussed in more detail herein, is the production of vector preparations that are essentially free of replication-competent virions. The following description briefly summarizes studies involving adeno-associated virus and AAV vectors, and then describes a number of novel improvements according to the present invention that are useful for efficiently generating high titer recombinant AAV vector (rAAV) preparations suitable for use in gene therapy.

Adeno-associated virus is a defective parvovirus that grows only in cells in which certain functions are provided by a co-infecting helper virus. General reviews of AAV may be found in, for example, Carter, 1989, *Handbook of Parvoviruses*, Vol. I, pp. 169–228, and Berns, 1990, *Virology*, pp. 1743–1764, Raven Press, (New York). Examples of co-infecting viruses that provide helper functions for AAV growth and replication are adenoviruses, herpesviruses and, in some cases, poxviruses such as vaccinia. The nature of the helper function is not entirely known but it appears that the helper virus indirectly renders the cell permissive for AAV replication. This belief is supported by the observation that AAV replication may occur at low efficiency in the absence of helper virus co-infection if the cells are treated with agents that are either genotoxic or that disrupt the cell cycle.

Although AAV may replicate to a limited extent in the absence of helper virus, under such conditions as noted above, more generally infection of cells with AAV in the absence of helper functions results in the proviral AAV genome integrating into the host cell genome. Unlike other viruses, such as many retroviruses, it appears that AAV generally integrates into a unique position in the human genome. Thus, it has been reported that, in human cells, AAV integrates into a unique position (referred to as an "AAV integration site") which is located on chromosome 19. See, e.g., Weitzman et al. (1994) *Proc. Natl. Acad. Sci. USA* 91: 5808–5812. If host cells having an integrated AAV are subsequently superinfected with a helper virus such as adenovirus, the integrated AAV genome can be rescued and replicated to yield a burst of infectious progeny AAV particles. A sequence at the AAV integration site, referred to as "P1", shares limited homology with the AAV inverted terminal repeat (ITR) sequence, exhibits Rep binding activity in a cell-free replication system, and is believed to be involved in both the integration and rescue of AAV. See, e.g., Weitzman et al., id., Kotin et al. (1992) *EMBO J.* 11:5071–5078, and Urcelay et al., *J. Virol.* 69: 2038–2046. The fact that integration of AAV appears to be efficient and site-specific makes AAV a useful vector for introducing genes into cells for uses such as human gene therapy.

AAV has a very broad host range without any obvious species or tissue specificity and can replicate in virtually any cell line of human, simian or rodent origin provided that an appropriate helper is present. AAV is also relatively ubiquitous and has been isolated from a wide variety of animal species including most mammalian and several avian species.

AAV is not associated with the cause of any disease. Nor is AAV a transforming or oncogenic virus, and integration of AAV into the genetic material of human cells generally does not cause significant alteration of the growth properties or morphological characteristics of the host cells. These properties of AAV also recommend it as a potentially useful human gene therapy vector because most of the other viral systems proposed for this application, such as retroviruses, adenoviruses, herpesviruses, or poxviruses, are disease-causing.

Although various serotypes of AAV are known to exist, they are all closely related functionally, structurally, and at the genetic level (see, e.g., Blacklow, 1988, pp. 165–174 of *Parvoviruses and Human Disease*, J. R. Pattison (ed.); and Rose, 1974, *Comprehensive Virology* 3: 1–61). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to inverted terminal repeats (ITRs). The similar infectivity patterns also suggest that the replication functions in each serotype are under similar regulatory control. Thus, although the AAV2 serotype was used in various illustrations of the present invention that are set forth in the Examples, general reference to AAV herein encompasses all AAV serotypes, and it is fully expected that the methods and compositions disclosed herein will be applicable to all AAV serotypes.

AAV particles comprise a proteinaceous capsid having three capsid proteins, VP1, VP2 and VP3, which enclose a DNA genome. The AAV2 DNA genome, for example, is a linear single-stranded DNA molecule having a molecular weight of about $1.5 \times 10^6$ daltons and a length of about 5 kb. Individual particles package only one DNA molecule strand, but this may be either the "plus" or "minus" strand. Particles containing either strand are infectious and replication occurs by conversion of the parental infecting single strand to a duplex form and subsequent amplification of a large pool of duplex molecules from which progeny single strands are displaced and packaged into capsids. Duplex or single-strand copies of AAV genomes can be inserted into bacterial plasmids or phagemids and transfected into adenovirus-infected cells; these techniques have facilitated the study of AAV genetics and the development of AAV vectors.

The AAV genome, which encodes proteins mediating replication and encapsidation of the viral DNA, is generally flanked by two copies of inverted terminal repeats (ITRs). In the case of AAV2, for example, the ITRs are each 145 nucleotides in length, flanking a unique sequence region of about 4470 nucleotides that contains two main open reading frames for the rep and cap genes (Srivastiva et al., 1983, *J. Virol.*, 45:555–564; Hermonat et al., 1984, *J. Virol.* 51:329–339; Tratschin et al., 1984, *J. Virol.,* 51:611–619). The AAV2 unique region contains three transcription promoters p5, p19, and p40 (Laughlin et al., 1979, *Proc. Natl. Acad. Sci. USA,* 76:5567–5571) that are used to express the rep and cap genes. The ITR sequences are required in cis and are sufficient to provide a functional origin of replication (ori), signals required for integration into the cell genome, and efficient excision and rescue from host cell chromosomes or recombinant plasmids. It has also been shown that the ITR can function directly as a transcription promoter in an AAV vector. See Carter et al., U.S. Pat. No. 5,587,308.

The rep and cap gene products are required in trans to provide functions for replication and encapsidation of viral genome, respectively. Again, using AAV2 for purposes of illustration, the rep gene is expressed from two promoters, p5 and p19, and produces four proteins. Transcription from p5 yields an unspliced 4.2 kb mRNA encoding a first Rep protein (Rep78), and a spliced 3.9 kb mRNA encoding a second Rep protein (Rep68). Transcription from p19 yields an unspliced mRNA encoding a third Rep protein (Rep52), and a spliced 3.3 kb mRNA encoding a fourth Rep protein (Rep40). Thus, the four Rep proteins all comprise a common internal region sequence but differ in their amino and carboxyl terminal regions. Only the large Rep proteins (i.e. Rep78 and Rep68) are required for AAV duplex DNA replication, but the small Rep proteins (i.e. Rep52 and Rep40) appear to be needed for progeny, single-strand DNA accumulation (Chejanovsky & Carter, 1989, *Virology* 173:120–128). Rep68 and Rep78 bind specifically to the hairpin conformation of the AAV ITR and possess several enzyme activities required for resolving replication at the AAV termini. Rep52 and Rep40 have none of these properties. Reports by C. Hölscher et al. (1994, *J. Virol.* 68:7169–7177; and 1995, *J. Virol.* 69:6880–6885) have suggested that expression of Rep78 or Rep 68 may in some circumstances be sufficient for infectious particle formation.

The Rep proteins, primarily Rep78 and Rep68, also exhibit pleiotropic regulatory activities including positive and negative regulation of AAV genes and expression from some heterologous promoters, as well as inhibitory effects on cell growth (Tratschin et al., 1986, *Mol. Cell. Biol.* 6:2884–2894; Labow et al., 1987, *Mol. Cell. Biol.,* 7:1320–1325; Khleifet al., 1991, *Virology,* 181:738–741). The AAV p5 promoter is negatively auto-regulated by Rep78 or Rep68 (Tratschin et al., 1986). Due to the inhibitory effects of expression of rep on cell growth, constitutive expression of rep in cell lines has not been readily achieved. For example, Mendelson et al. (1988, *Virology,* 166:154–165) reported very low expression of some Rep proteins in certain cell lines after stable integration of AAV genomes.

The capsid proteins VP1, VP2, and VP3 share a common overlapping sequence, but VP1 and VP2 contain additional amino terminal sequences. All three proteins are encoded by the same cap gene reading frame typically expressed from a spliced 2.3 kb mRNA transcribed from the p40 promoter. VP2 and VP3 can be generated from this mRNA by use of alternate initiation codons. Generally, transcription from p40 yields a 2.6 kb precursor mRNA which can be spliced at alternative sites to yield two different transcripts of about 2.3 kb. VP2 and VP3 can be encoded by either transcript (using either of the two initiation sites), whereas VP1 is encoded by only one of the transcripts. VP3 is the major capsid protein, typically accounting for about 90% of total virion protein. VP1 is coded from a minor mRNA using a 3' donor site that is 30 nucleotides upstream from the 3' donor used for the major mRNA that encodes VP2 and VP3. All three proteins are required for effective capsid production. Mutations which eliminate all three proteins (Cap-negative) prevent accumulation of single-strand progeny AAV DNA, whereas mutations in the VP1 amino-terminus ("Lip-negative" or "Inf-negative") can permit assembly of single-stranded DNA into particles but the infectious titer is greatly reduced.

The genetic analysis of AAV described above was largely based upon mutational analysis of AAV genomes cloned into bacterial plasmids. In early work, molecular clones of infectious genomes of AAV were constructed by insertion of double-strand molecules of AAV into plasmids by procedures such as GC-tailing (Samulski et al., 1982, *Proc. Natl. Acad. Sci. USA,* 79:2077–2081), addition of synthetic linkers containing restriction endonuclease cleavage sites (Laughlin et al., 1983, *Gene,* 23:65–73) or by direct, blunt-end ligation (Senapathy & Carter, 1984, *J. Biol. Chem.,* 259:4661–4666). Transfection of such AAV recombinant plasmids into mammalian cells that were also infected with an appropriate helper virus, such as adenovirus, resulted in rescue and excision of the AAV genome free of any plasmid sequence, replication of the rescued genome and generation of progeny infectious AAV particles. This provided the basis for performing genetic analysis of AAV as summarized above and permitted construction of AAV transducing vectors.

There are at least two desirable features of any AAV vector designed for use in human gene therapy. The first is that the transducing vector be generated at titers sufficiently high to be practicable as a delivery system. This is especially important for gene therapy strategies aimed at in vivo delivery of the vector. For example, it is likely that for many desirable applications of AAV vectors, such as treatment of cystic fibrosis by direct in vivo delivery to the airway, the desired dose of transducing vector may be from $10^8$ to $10^{10}$, or, in some cases, in excess of $10^{10}$ particles. Secondly, the vector preparations are preferably essentially free of wild-type AAV virus (or any replication-competent AAV). The attainment of high titers of AAV vectors has been difficult for several reasons including preferential encapsidation of wild-type AAV genomes (if they are present or generated by recombination), and the difficulty in generating sufficient complementing functions such as those provided by the wild-type rep and cap genes. Useful cell lines expressing such complementing functions have been especially difficult to generate, in part because of pleiotropic inhibitory functions associated with the rep gene products. Thus, cell lines in which the rep gene is integrated and expressed may grow slowly or express rep at very low levels.

Based on genetic analyses described above, the general principles of AAV vector construction have been described. See, for example, Carter, 1992, *Current Opinions in Biotechnology,* 3:533–539; Muzyczka, 1992, *Curr. Topics in Microbiol. and Immunol.,* 158:97–129. AAV vectors are generally constructed in AAV recombinant plasmids by substituting portions of the AAV coding sequence with foreign DNA to generate a recombinant AAV (rAAV) vector or "pro-vector". It is well established in the AAV literature that, in the vector, the terminal (ITR) portions of the AAV sequence must be retained intact because these regions are required in cis for several functions, including excision from the plasmid after transfection, replication of the vector genome and integration and rescue from a host cell genome. In some situations, providing a single ITR may be sufficient to carry out the functions normally associated with two wild-type ITRs (see, e.g., Samulski et al., WO 94/13788, published 23 Jun. 1994).

As described in the art, AAV ITRs generally consist of a palindromic hairpin (HP) structure and a 20-nucleotide region, designated the D-sequence, that is not involved in the HP formation. Wang et al. identified AAV ITR sequences required for rescue, replication and encapsidation of the AAV genome (Wang et al., 1996, J. Virol. 70:1668–1677). Wang et al. (1996) reported the following: (i) two HP structures and one D-sequence are sufficient for efficient rescue and preferential replication of the AAV DNA, (ii) two HP structures alone allow a low level rescue and replication of the AAV DNA, but rescue and replication of the AAV vector DNA sequences also occur in the absence of the of the D-sequences, (iii) one HP structure and two D-sequences, but not one HP structure and one D-sequence, also allow rescue and replication of the AAV as well as the vector DNA sequences, (iv) one HP structure alone or two D-sequences but not one D-sequence alone allows replication of full length plasmid DNA but no rescue of the AAV genome occurs, (v) no rescue-replication occurs in the absence of the HP structures and D-sequence, (vi) in the absence of the D-sequences, the HP structures are insufficient for successsful encapsidation of the AAV genomes, and (vii) the AAV genomes containing only one ITR structure can be packaged into biologically active virions. Thus, Wang et al. conclude that the D-sequence plays a crucial role in the efficient rescue and selective replication and encapsidation of the AAV genome. Subsequent studies published by this group suggested that the first 10 nucleotides of the D-sequence proximal to the hairpin structure of the ITR are necessary and sufficient for optimal rescue and replication of the AAV genome (Wang et al., 1997, *J. Virol.* 71:3077–3082). Thus, this work identifies the D-sequence as required for packaging of the AAV genome.

The vector can then be packaged into an AAV particle to generate an AAV transducing virus by transfection of the vector into cells that are infected by an appropriate helper virus such as adenovirus or herpesvirus; provided that, in order to achieve replication and encapsidation of the vector genome into AAV particles, the vector must generally be complemented for any AAV functions required in trans, particularly rep and cap, that were deleted in construction of the vector.

Such AAV vectors are among a small number of recombinant virus vector systems which have been shown to have utility as in vivo gene transfer agents (reviewed in Carter, 1992; Muzyczka, 1992) and thus are potentially of great importance for human gene therapy. AAV vectors are capable of high-frequency transduction and expression in a variety of cells including cystic fibrosis (CF) bronchial and nasal epithelial cells (see, e.g., Flotte et al., 1992, *Am. J. Respir. Cell Mol. Biol.* 7:349–356; Egan et al., 1992, *Nature*, 358:581–584; Flotte et al., 1993a, *J. Biol. Chem.* 268:3781–3790; and Flotte et al., 1993b, *Proc. Natl. Acad. Sci. USA*, 93:10163–10167); human bone marrow-derived erythroleukemia cells (see, e.g., Walsh et al., 1992, *Proc. Natl. Acad. Sci. USA*, 89:7257–7261); as well as brain, eye and muscle cells. AAV may not require active cell division for transduction and expression which would be another clear advantage over retroviruses, especially in tissues such as the human airway epithelium where most cells are terminally differentiated and non-dividing.

There is a significant need for methods that can be used to efficiently generate recombinant vectors encapsidated in AAV particles that are essentially free of wild-type or other replication-competent AAV; and a corresponding need for cell lines that can be used to effectively generate such recombinant vectors. The present invention provides methods, compositions, and cells for the production of high-titer, AAV particle-encapsidated, recombinant vector preparations.

All publications and patent applications cited herein are hereby incorporated by reference in their entirety.

SUMMARY OF THE INVENTION

The present invention provides compositions and methods that, when operably linked in cis to a heterologous gene, promote encapsidation of the heterologous gene into an AAV particle, wherein the in cis encapsidation function is provided by a polynucleotide (i.e., an encapsidation element) other than an AAV ITR or preferably, other than a D-sequence of an AAV ITR. In particular, the inventors have found that by using one or more non-AAV ITR encapsidation elements in operable linkage with a heterologous gene, and additionally providing AAV rep and cap gene products, it is possible to obtain encapsidation of the heterologous gene in an AAV particle. As described and exemplified herein, heterologous gene sequences in operable linkage with a non-AAV ITR encapsidation element can be integrated into the chromosome of a host cell or can be maintained extrachromosomally as an episome. The methods and compositions of the present invention can be used to generate stable producer cells that are capable of supporting production of a very large burst of AAV particles containing a recombinant vector (recombinant polynucleotide), upon infection with a suitable helper virus (such as adenovirus) or provision of helper functions.

Accordingly, in one embodiment, the invention provides an isolated recombinant polynucleotide sequence comprising a heterologous gene operably linked to an encapsidation element other than an AAV ITR or a D-sequence of an AAV ITR. In some of these embodiments, the encapsidation element is a P1 element, as described herein.

In additional embodiments, the invention provides methods for producing high-titer stocks of recombinant vectors containing a foreign gene encapsidated in an AAV particle, by providing a mammalian cell which produces AAV rep and cap gene products and which contains the recombinant vector comprising a heterologous gene operably linked to an encapsidation element other than an AAV ITR or preferably, other than a D-sequence of an AAV ITR.

The invention also provides compositions and methods for producing cell lines which comprise a recombinant vector comprising a heterologous gene operably linked to an encapsidation element other than an AAV ITR or a D-sequence of an AAV ITR, which synthesize AAV rep and cap gene products, and which encapsidate the recombinant vector in an AAV particle; cells and cell lines produced thereby; compositions and methods for high-efficiency packaging of a recombinant vector containing a heterologous gene; and recombinant vectors packaged according to the method of the invention.

BRIEF DESCRIPTION OF THE DRAWINGS

FIG. 1 (SEQ ID NO:8) depicts a nucleotide sequence of a SmaI fragment comprising a P1 element. SmaI sites are underlined.

FIG. 2 (SEQ ID NOS:9–10) depicts a nucleotide sequence alignment between the nucleotide sequence of a 62-nucleotide P1 encapsidation element (upper line) and nucleotides 145–79 of AAV2 ITR (lower line). The terminal resolution site is underlined, a Rep68/Rep78 binding site is indicated in bold, and the 20-nucleotide D sequence of the AAV2 ITR is italicized and in bold. Vertical lines indicate nucleotide identity. A gap, indicated by dashes, of five nucleotides was introduced into the P1 sequence for optimal alignment.

FIG. 3 (SEQ ID NOS:9–10, 12–16) depicts nucleotide sequence alignments between the nucleotide sequence of a 62-nucleotide P1 encapsidation element (upper lines) and nucleotides of ITRs of various AAV serotypes (lower lines). The terminal resolution site is underlined, a Rep68/Rep78 binding site is indicated in bold and vertical lines indicate nucleotide identity. As with the alignment with the AAV2 ITR shown in FIG. 2 (SEQ ID NOS:9–10), a gap, indicated by dashes, was introduced into the P1 sequences for optimal alignment.

MODES FOR CARRYING OUT THE INVENTION

Figure 4:
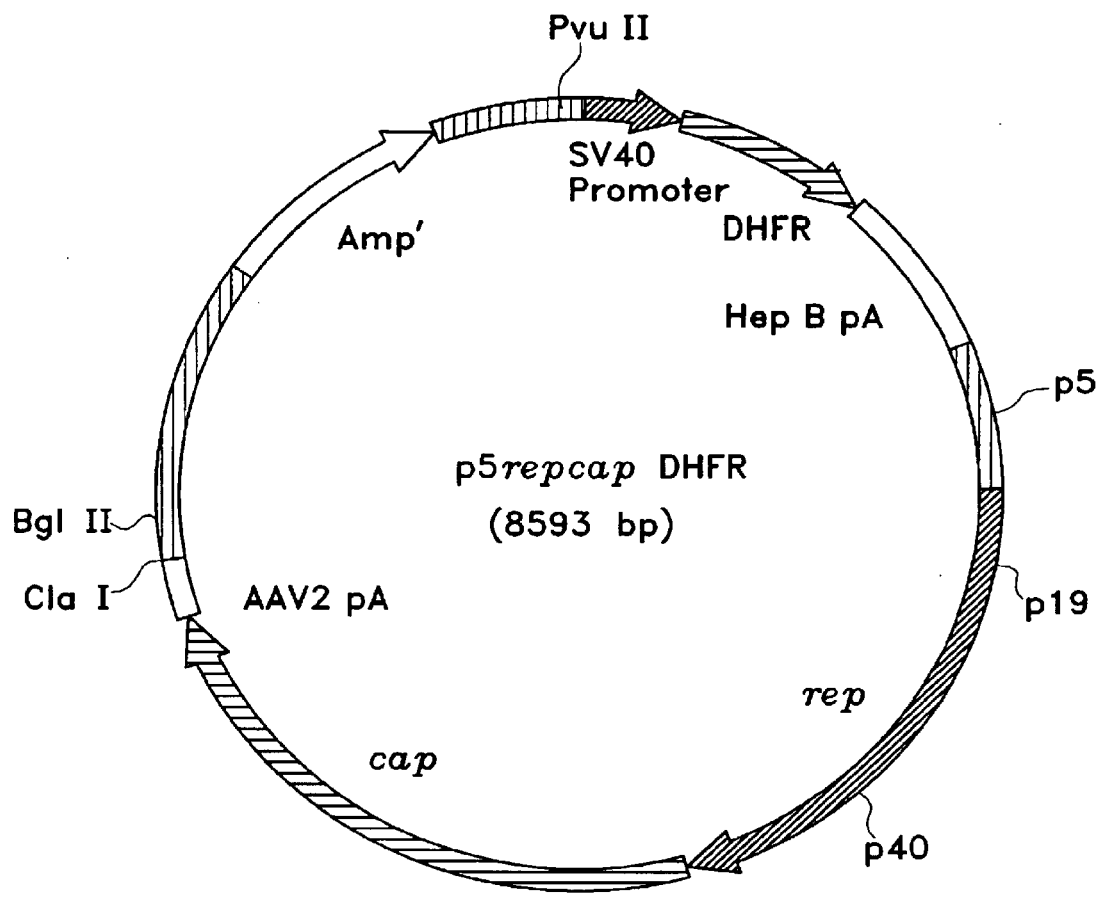
FIG. 4 shows a map of the p5repcapDHFR plasmid.

A basic challenge in the area of gene therapy is the development of strategies for efficient gene delivery to cells and tissues in vivo. One strategy involves the use of recombinant vectors encapsidated in AAV particles. Recombinant AAV particle-packaged vectors are recombinant constructs comprising sequences required in cis for vector packaging, along with heterologous polynucleotide(s) encoding a protein or function of interest. Recombinant vectors packaged in AAV particles are potentially powerful tools for human gene therapy, and in general are useful for introducing a polynucleotide into a cell.

Although recombinant vectors packaged in AAV particles are capable of in vivo gene delivery, for example in the respiratory tract, high titers of such vectors are necessary to allow the delivery of a sufficiently high multiplicity of vector in a minimal volume. Consequently, optimal packaging methodology is of central importance for AAV-mediated gene therapy approaches. Packaging of recombinant vectors into AAV particles is mediated in part by the products of two AAV genes: rep (replication proteins) and cap (capsid proteins), which can be provided separately in trans. Previously, it was believed that, in addition to the rep and cap gene products provided in trans, an ITR was necessary to provide encapsidation functions in cis. In addition, it was previously shown that a 20-nucleotide portion of the AAV ITR, known as the "sequence", plays a crucial role in the efficient rescue and selective replication and encapsidation of the AAV genome (Wang et al., 1996, *J. Virol.* 70:1668–1677). The inventors of this invention have made the surprising discovery that sequences other than an AAV ITR or a D-sequence of an AAV ITR can provide encapsidation function in cis.

The inventors of the instant invention have previously shown (in co-owned International Patent Application No. PCT/US98/21938, the contents of which are incorporated by reference herein) that P1 or a P1-like element provides for controlled amplification of DNA comprising the P1 or P1-like element amplifiably linked to AAV rep and cap genes, thereby providing increased template levels for synthesis of AAV packaging proteins. It has now been discovered that P1 or a P1-like element can promote encapsidation of an operably linked polynucleotide.

The present invention provides methods, polynucleotides, and packaging cells for producing stocks of recombinant vector encapsidated in an AAV particle. A heterologous polynucleotide is operably linked to an encapsidation element other than an AAV ITR or a D-sequence of an AAV ITR. In some embodiments, the activating element is directly or indirectly triggered by the user when it is desired to initiate vector production, preferably by infection with helper virus or provision of helper function. The use of the P1 sequence of human chromosome 19 is exemplary in these respects.

Without wishing to be bound by theory, it appears that upon infection or provision of helper function, the p5 promoter is turned on to some degree, resulting in the synthesis of some Rep protein, which may then, by acting via the encapsidation element, trigger an encapsidation event by which the linked gene(s) are encapsidated in an AAV particle. The encapsidation element, exemplified by P1, can thus promote encapsidation of a gene or genes to which it is linked.

The invention also provides recombinant vectors comprising a heterologous gene operably linked to an encapsidation element other than an AAV ITR or a D-sequence of an AAV ITR. Preferably, the recombinant vector comprising the heterologous gene have a size no greater than the upper size limit for packaging into an AAV particle, including, but not limited to, a size of approximately 5 kb. These vectors, when encapsidated into an AAV particle, are useful for introducing heterologous genes into a cell.

General Methods

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, Fritsch, and Maniatis, *Molecular Cloning: A Laboratory Manual*, Second Edition (1989); *Oligonucleotide Synthesis* (M. J. Gait Ed., 1984); Animal Cell Culture (R. I. Freshney, Ed., 1987); the series *Methods in Enzymology* (Academic Press, Inc.); *Gene Transfer Vectors for Mammalian Cells* (J. M. Miller and M. P. Calos eds. 1987); *Handbook of Experimental Immunology*, (D. M. Weir and C. C. Blackwell, Eds.); *Current Protocols in Molecular Biology* (F. M. Ausubel, R. Brent, R. E. Kingston, D. D. Moore, J. G. Seidman, J. A. Smith, and K. Struhl, eds., 1987, and updates); and *Current Protocols in Immunology* (J. E. Coligan, A. M. Kruisbeek, D. H. Margulies, E. M. Shevach and W. Strober, eds., 1991).

All patents, patent applications, and publications mentioned herein, both supra and infra, are hereby incorporated herein by reference.

Definitions

As used in the specification and claims, the singular form "a", "an" and "the" include plural references unless the context clearly dictates otherwise. For example, the term "a cell" includes a plurality of cells, including mixtures thereof.

The terms "polypeptide", "peptide" and "protein" are used interchangeably to refer to polymers of amino acids of any length. These terms also include proteins that are post-translationally modified through reactions that include, but are not limited to, glycosylation, acetylation and phosphorylation.

"Polynucleotide" refers to a polymeric form of nucleotides of any length, either ribonucleotides or deoxyribonucleotides, or analogs thereof. This term refers only to the primary structure of the molecule. Thus, double- and single-stranded DNA, as well as double- and single-stranded RNA are included. It also includes modified polynucleotides such as methylated or capped polynucleotides.

A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity can be determined using software programs known in the art, for example those described in Current Protocols in Molecular Biology (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: http://www.ncbi.nlm.nih.gov/BLAST.

A "gene" refers to a polynucleotide containing at least one open reading frame that is capable of encoding a particular protein after being transcribed and translated.

As used herein, "an encapsidation element other than an AAV ITR or a D sequence of an AAV ITR", used interchangeably herein with "a packaging signal other than an AAV ITR or a sequence of an AAV ITR" and "a non-AAV ITR encapsidation element", intends a polynucleotide sequence which, when operably linked in cis to a heterologous gene, promotes (or enhances or increases) encapsidation of the heterologous gene into an AAV particle, when AAV rep and cap gene products are provided in trans. For the purposes of the present invention, an encapsidation element is not an AAV ITR or a sequence of an AAV ITR. AAV ITRs and their sequences are known in the art, and those skilled in the art, given the guidance provided herein, can readily determine whether a given encapsidation element is an AAV ITR or an AAV ITR sequence or a non-AAV ITR encapsidation element.

As used herein, the terms "heterologous gene operably linked to an encapsidation element", "heterologous polynucleotide operably linked to an encapsidation element", used interchangeably herein, refer to a polynucleotide sequence which is not normally associated in nature with a given encapsidation element.

In the context of the physical linkage between a heterologous gene and an encapsidation element, the term "operably linked", as used herein, intends a physical and/or functional arrangement of a heterologous gene and an encapsidation element that permits the encapsidation element to function in cis, in the presence of AAV rep and cap gene products, to encapsidate the heterologous gene in an AAV particle. Methods of determining whether a given encapsidation element is "operably linked" to a given heterologous gene are known in the art, and are described herein, and include, but are not limited to, measuring the number of DNAse-resistant particles (DRPs) which contain the heterologous gene, as determined, for example, by hybridization analysis.

The term "ITR" refers to an inverted terminal repeat at either end of the AAV genome. Generally, AAV ITRs are approximately 145 nucleotides long. The first 125 bases of the ITR can form a shaped hairpin structure which is composed of two small internal palindromes flanked by a larger palindrome (Muzycska et al., 1992). ITRs have been identified as being involved in AAV DNA replication and rescue, or excision, from prokaryotic plasmids (Samulski et al., 1983, Cell 33:135–143, Samulski et al., 1987, J. Virol. 61:3096–3101; Senapathy et al., 1984, J. Mol. Biol. 179:1–20; Gottlieb and Muzyczka, 1988, Mol. Cell. Biol. 6:2513–2522).

As used herein, the term "D sequence of an AAV ITR" refers to a specific sequence element within an AAV ITR which has been identified as playing a role in rescue, selective replication and encapsidation of the AAV genome as described, for example, in Wang et al., 1996 and Wang et al., 1997. The D sequence of an AAV2 ITR is illustrated in FIG. 2 (SEQ ID NOS:9–10) and, as used herein, a "D sequence of an AAV ITR" refers to the D sequence of AAV2 ITR as well as D sequences of the ITRs of other AAV serotypes.

A "transcriptional regulatory sequence" as used herein, refers to a nucleotide sequence that controls the transcription of a gene or coding sequence to which it is operably linked. Transcriptional regulatory sequences of use in the present invention generally include at least one transcriptional promoter and may also include one or more enhancers and/or terminators of transcription.

A "promoter," as used herein, refers to a nucleotide sequence that directs the transcription of a gene or coding sequence to which it is operably linked.

"Operably linked" refers to an arrangement of two or more components, wherein the components so described are in a relationship permitting them to function in a coordinated manner. By way of illustration, a transcriptional regulatory sequence or a promoter is operably linked to a coding sequence if the transcriptional regulatory sequence or promoter promotes transcription of the coding sequence. An operably linked transcriptional regulatory sequence is generally joined in cis with the coding sequence, but it is not necessarily directly adjacent to it.

"Recombinant," refers to a genetic entity distinct from that generally found in nature. As applied to a polynucleotide or gene, this means that the polynucleotide is the product of various combinations of cloning, restriction and/or ligation steps, and other procedures that result in a construct that is distinct from a polynucleotide found in nature.

"Heterologous" means derived from a genotypically distinct entity from that of the rest of the entity to which it is compared. For example, a polynucleotide introduced by genetic engineering techniques into a different cell type is a heterologous polynucleotide (and, when expressed, can encode a heterologous polypeptide). Similarly, a transcriptional regulatory sequence or promoter that is removed from its native coding sequence and operably linked to a different coding sequence is a heterologous transcriptional regulatory sequence or promoter.

A "vector", as used herein, refers to a recombinant plasmid or virus that comprises a polynucleotide to be delivered into a host cell, either in vitro or in vivo. The polynucleotide to be delivered, sometimes referred to as a "target polynucleotide," "transgene", or "gene of interest" may comprise a coding sequence of interest in gene therapy (such as a gene encoding a protein of therapeutic interest) and/or a selectable or detectable marker.

A "replicon" refers to a polynucleotide comprising an origin of replication which allows for replication of the polynucleotide in an appropriate host cell. Examples of replicons include episomes (including plasmids), as well as chromosomes (such as the nuclear or mitochondrial chromosomes).

An "origin," "replication origin," "ori-like sequence" or "ori element" is a nucleotide sequence involved in one or more aspects of initiation of DNA replication, such as, for example, binding of replication initiation factors, unwinding of the DNA duplex, primer formation, and/or template-directed synthesis of a complementary strand. As discussed in detail herein and in the art, ori-like sequences can generally be found in any polynucleotide that is naturally replicated, including plasmids and viruses, as well as prokaryotic, mitochondrial and chloroplast genomes and eukaryotic chromosomes. Such ori-like sequences can be identified genetically (i.e., replication-defective mutants, ars sequences) or functionally (ie., through biochemical assay, electron microscopy, etc.), as is known in the art.

"Stable integration" of a polynucleotide into a cell means that the polynucleotide has been integrated into a replicon that tends to be stably maintained in the cell. Although episomes such as plasmids can sometimes be maintained for many generations, genetic material carried episomally is generally more susceptible to loss than chromosomally-integrated material. However, maintenance of a polynucleotide can often be effected by incorporating a selectable marker into or adjacent to a polynucleotide, and then maintaining cells carrying the polynucleotide under selective pressure. In some cases, sequences cannot be effectively maintained stably unless they have become integrated into a chromosome; and, therefore, selection for retention of a sequence comprising a selectable marker can result in the selection of cells in which the marker has become stably-integrated into a chromosome. Antibiotic resistance genes can be conveniently employed as such selectable markers, as is well known in the art. Typically, stably-integrated polynucleotides would be expected to be maintained on average for at least about twenty generations, preferably at least about one hundred generations, still more preferably they would be maintained permanently. The chromatin structure of eukaryotic chromosomes can also influence the level of expression of an integrated polynucleotide. Having the genes carried on stably-maintained episomes can be particularly useful where it is desired to have multiple stably-maintained copies of a particular gene. The selection of stable cell lines having properties that are particularly desirable in the context of the present invention are described and illustrated below.

"AAV" is adeno-associated virus. Adeno-associated virus is a defective parvovirus that grows only in cells in which certain functions are provided by a co-infecting helper virus. General reviews of AAV may be found in, for example, Carter, 1989, *Handbook of Parvoviruses*, Vol. 1, pp. 169–228, and Berns, 1990, *Virology*, pp. 1743–1764, Raven Press, (New York). The AAV2 serotype was used in some of the illustrations of the present invention that are set forth in the Examples. However, it is fully expected that these same principles will be applicable to other AAV serotypes since it is now known that the various serotypes are quite closely related—both functionally and structurally, even at the genetic level (see, e.g., Blacklow, 1988, pp. 165–174 of *Parvoviruses and Human Disease*, J. R. Pattison (ed.); and Rose, 1974, *Comprehensive Virology* 3: 1–61). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to inverted terminal repeats (ITRs). The similar infectivity patterns also suggest that the replication functions in each serotype are under similar regulatory control.

A "recombinant AAV vector" (or "rAAV vector") refers to a vector comprising one or more polynucleotide sequences of interest, genes of interest or "transgenes" that are flanked by AAV inverted terminal repeat sequences (ITRs). Such rAAV vectors can be replicated and packaged into infectious viral particles when present in a host cell that has been infected with a suitable helper virus and that is expressing AAV rep and cap gene products (i.e. AAV Rep and Cap proteins). When an rAAV vector is incorporated into a larger polynucleotide (e.g. in a chromosome or in another vector such as a plasmid used for cloning or transfection), then the rAAV vector is typically referred to as a "pro-vector" which can be "rescued " by replication and encapsidation in the presence of AAV packaging functions and necessary helper functions.

As used herein, a recombinant vector to be packaged (encapsidated) in an AAV particle intends a vector comprising one or more heterologous polynucleotide sequences, heterologous genes or "transgenes" that are operably linked to an encapsidation element other than an AAV ITR or a D-sequence of an AAV ITR. Such recombinant vectors can be replicated and packaged into infectious AAV particles when present in a host cell that has been infected with a suitable helper virus (or provided with helper function(s)) and that synthesizes AAV rep and cap gene products (i.e. AAV Rep and Cap proteins).

A "helper virus" for AAV refers to a virus that allows AAV (which is a "defective" parvovirus) to be replicated and packaged by a host cell. A number of such helper viruses have been identified, including adenoviruses, herpesviruses and 1.5 poxviruses such as vaccinia. The adenoviruses encompass a number of different subgroups, although Adenovirus type 5 of subgroup (Ad5) is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC. "Helper function" refers to the activity provided by the helper virus that allows replication and packaging of an AAV genome, or any equivalent activity. Helper functions are also believed to stimulate transcription of some AAV promoters, including p5, and may enhance processivity of replication in cells in which helper functions are expressed.

"Packaging" as used herein refers to a series of subcellular events that results in the assembly and encapsidation of all or part of a recombinant vector comprising one or more encapsidation elements other than an AAV ITR or and AAV ITR D-sequence. Thus, when a recombinant vector comprising an encapsidation element other than an AAV ITR or its sequence, is introduced into a packaging cell, or packaging cell line, under appropriate conditions, it can be assembled into a viral particle. Functions associated with packaging of viral vectors, particularly AAV vectors, are described herein and in the art.

AAV "rep" and "cap" genes are genes encoding replication and encapsidation proteins, respectively. AAV rep and cap genes have been found in all AAV serotypes examined, and are described herein and in the references cited. In wild-type AAV, the rep and cap genes are generally found adjacent to each other in the viral genome (i.e. they are "coupled" together as adjoining or overlapping transcriptional units), and they are generally conserved among AAV serotypes. AAV rep and cap genes are also individually and collectively referred to herein as "AAV packaging genes." AAV packaging genes that have been modified by deletion or point mutation, or which have been subdivided into components which can be rejoined by recombination (e.g., as described in co-owned International Patent Application No. PCT/US97/23247, the disclosure of which is hereby incorporated by reference), may also be used in the present invention. AAV packaging genes can also be operably linked to other transcriptional regulatory sequences, including promoters, enhancers and polyadenylation ("polyA") sequences (which additional transcriptional regulatory sequences can also be heterologous). An "AAV packaging cassette" is a recombinant construct which includes one or more AAV packaging genes.

"Efficiency" when used in describing a cell line refers to certain useful attributes of the line; in particular, the growth rate, and (for packaging cell lines) the number of virus particles produced per cell. "Efficient growth" of a packaging cell line refers to the effective growth rate of the packaging cell, related to a comparable parental-type cell (i.e., a cell that does not carry an introduced AAV packaging gene). Preferably, the relative growth rate is at least 20% of the parental type, more preferably, 40%, more preferably, 80%, still more preferably, 90% and, most preferably, 100%. "High efficiency packaging" indicates production of at least about 100 viral particles per cell, more preferably at least about 1,000 viral particles per cell, still more preferably at least about 10,000 viral particles per cell. "High safety packaging" indicates that, of the recombinant AAV viral particles produced, fewer than about 1 in $10^6$ are replication-competent AAV viral particles, preferably fewer than about 1 in $10^8$ are replication-competent, more preferably fewer than about 1 in $10^{10}$ are replication-competent, still more preferably fewer than about 1 in $10^{12}$ are replication-competent, most preferably none are replication-competent. Preferred packaging cells of the present invention exhibit combinations of such high efficiency and high safety.

"Host cells", "cell lines", "cell cultures", "packaging cell line" and other such terms denote higher eukaryotic cells, preferably mammalian cells, most preferably human cells, useful in the present invention. These cells can be used as recipients for recombinant vectors, viruses or other transfer polynucleotides, and include the progeny of the original cell that was transduced. It is understood that the progeny of a single cell may not necessarily be completely identical (in morphology or in genomic complement) to the original parent cell.

A "therapeutic gene", "target polynucleotide", "transgene", "gene of interest", "heterologous gene", "heterologous polynucleotide" and the like generally refer to a gene or genes to be transferred using a vector. Typically, in the context of the present invention, such genes are located within a recombinant vector (which vector comprises the heterologous gene and one or more encapsidation elements other than an AAV ITR or its sequence) for packaging in an AAV particle. Target polynucleotides can be used in this invention to generate recombinant vectors for a number of different applications. Such polynucleotides include, but are not limited to: (i) polynucleotides encoding proteins useful in other forms of gene therapy to relieve deficiencies caused by missing, defective or sub-optimal levels of a structural protein or enzyme; (ii) polynucleotides that are transcribed into anti-sense molecules; (iii) polynucleotides that are transcribed into decoys that bind transcription or translation factors; (iv) polynucleotides that encode cellular modulators such as cytokines; (v) polynucleotides that can make recipient cells susceptible to specific drugs, such as the herpes virus thymidine kinase gene; (vi) polynucleotides for cancer therapy, such as E1A tumor suppressor genes or p53 tumor suppressor genes for the treatment of various cancers, (vii) polynucleotides that encode antigens or antibodies and (viii) polynucleotides that encode viral proteins, including, but not limited to, AAV Rep and Cap proteins. To effect expression of the transgene in a recipient host cell, it is preferably operably linked to a promoter or other such transcriptional regulatory sequence, either its own or a heterologous promoter. A large number of suitable promoters are known in the art, the choice of which depends on the desired level of expression of the target polynucleotide; whether one wants constitutive expression, inducible expression, cell-specific or tissue-specific expression, etc. The recombinant vector may also contain a selectable marker.

An "activating element" is a sequence that responds to the presence of an activation signal by amplifying (i.e., replicating the sequences) to which it is amplifiably linked. A preferred activating element is the P1 element and preferred activation signals include AAV helper functions (as exemplified by adenovirus E1A function) or their equivalents. As used herein, two sequences, one of which is an activating element, are "amplifiably linked" when they are in sufficient proximity to each other that replication initiating from the activating element results in amplification (i.e., increased copy number) of the other sequence. Preferably, the copy number of the amplified sequence is amplified 2-fold or greater, more preferably, 10-fold or greater, still more preferably, 20-fold or greater. It is to be noted that the ability of an activating element to amplify an amplifiably-linked sequence will be influenced by the degree of processivity of replication initiating from the activating element. Thus, factors that enhance processivity of replication will tend to increase the effective level of amplification of a sequence that is amplifiably linked to an activating element. In the context of the present invention, infection with adenovirus, or provision of equivalent helper function, may enhance processivity of replication as well as initiating amplification.

Encapsidation Elements for Use in Recombinant Vectors, Packaging Cells, and Methods of the Invention The present inventors have discovered that non-AAV ITR encapsidation elements such as the P1 sequence (normally found on human chromosome 19), when operably linked to one or more heterologous genes, in a mammalian cell which synthesizes AAV rep and cap gene products, can promote encapsidation of the linked heterologous gene into an AAV particle. In particular, when a recombinant vector of the present invention comprising an encapsidation element operably linked to a heterologous gene is provided in a mammalian cell which synthesizes AAV rep and cap gene products, under suitable conditions, including the provision of helper virus or helper function, high titers of AAV particles containing the recombinant vector are produced by the host cells. P1 exemplifies a class of encapsidation elements possessing, among other properties, activatable encapsidation function, that is useful in the generating recombinant vectors encapsidated in an AAV particle.

The methods and compositions of the invention will therefore utilize recombinant DNA constructs wherein a heterologous gene is operably linked to one or more encapsidation elements. The presently preferred encapsidation elements are exemplified by P1 and P1-like elements that exhibit functional properties related to encapsidation functions normally associated with AAV ITRs. Most preferred are elements that act as helper function-inducible encapsidation elements.

The P1 element contains at least two distinct sequence motifs, a site at which Rep proteins can bind, known as the "Rep-binding motif" (or "Rep-binding site" or "RB site") and a terminal resolution site ("trs"), at which bound Rep protein can nick the DNA (see FIG. 2 (SEQ ID NOS:9–10)). During AAV replication, it is believed that Rep protein binds within the AAV inverted terminal repeat and catalyzes the formation of a nick (at the terminal resolution site), resulting in covalent attachment of Rep protein to the newly generated 5' end. The 3' end of the nick serves as a primer for AAV DNA synthesis. Subsequently, operably linked polynucleotides are encapsidated unidirectionally. Further, as shown in Example 3, either of both strands of a double-stranded polynucleotide can be encapsidated. In the Examples, encapsidation of a given polynucleotide into AAV particles is determined by measuring DNAse-resistant particles, and further by determining the polynucleotide contents of the DRPs by hybridization with a labelled probe complementary to the polynucleotide. These methods can be used as an assay to identify additional encapsidation elements.

Weitzman et al. ((1994) Proc. Natl. Acad. Sci. USA 91:5808–5812) reported that a 109-base pair SmaI fragment (FIG. 1 (SEQ ID NO:8)), designated P1, at the site of AAV integration into the human genome specifically binds Rep 68 and Rep78 proteins. A P1 element for use in the present invention can comprise this 109-bp fragment. However, as discussed below, portions of this 109-bp fragment can function to encapsidate an operably linked polynucleotide. In addition, longer fragments from the AAV integration site which comprise this P1 element can also be used. Further, variants of this sequence can be used to promote encapsidation of an operably linked polynucleotide sequence.

As shown FIG. 2 (SEQ ID NOS:9–10), a 62-nucleotide encapsidation element, which is a sub-fragment of the 109-bp P1 element described above, shares about 47% nucleotide sequence identity when aligned with an AAV2 ITR from nucleotide 145 to 79 (Muzyczka, 1992), where a 5-nucleotide gap is introduced between nucleotides 32 and 33 of the P1 element shown in FIG. 2 (SEQ ID NOS:9–10).

As was done with the AAV2 ITR sequence, ITR sequences from other AAV serotypes have also been aligned with the 62-nucleotide P1 encapsidation element (FIG. 3 (SEQ ID NOS:9–10, 12–16))). AAV ITR sequences were taken from Xiao et al., 1999, J. Virol. 73:3994–4003; Muramatsu et al., 1996, Virology 221:208–217; Chiorini et al., 1997, J. Virol. 71:6823–6833 and Chiorini et al., 1999, J. Virol. 73:4293–4298. As depicted in FIG. 3 (SEQ ID) NOS:9–10, 12–16), the P1 element shares about 42% nucleotide sequence identity when aligned with an AAV1 ITR, the P1 element shares about 44% nucleotide sequence identity when aligned with an AAV3 ITR, the P1 element shares about 45% nucleotide sequence identity when aligned with an AAV4 ITR, the P1 element shares about 53% nucleotide sequence identity when aligned with an AAV5 ITR and the P1 element shares about 39% nucleotide sequence identity when aligned with an AAV6 ITR.

In some embodiments, a non-AAV ITR encapsidation element shares at least about 25 to about 30%, more preferably at least about 30 to about 40%, more preferably at least about 40 to about 45%, more preferably at least about 45 to about 47%, more preferably at least about 47 to about 53%, more preferably from at least about 53 to about 60%, more preferably at least about 60% to about 70%, more preferably at least about 70% to about 80%, more preferably at least about 80% to about 90%, even more preferably at least about 90% or more sequence identity with the 62-nucleotide P1 element shown in FIG. 2 (SEQ ID NOS:9–10). In some embodiments, recombinant vectors of the invention comprise one or more P1 elements, one or both of which have the sequence of the P1 element shown in FIG. 2 (SEQ ID NOS:9–10).

In some embodiments, a non-AAV ITR encapsidation element comprises a binding site for AAV Rep68/Rep78 proteins. In some of these embodiments, the Rep68/Rep78 binding site has the nucleotide sequence 5' GCX-CGCTCGCTCGCTX (SEQ ID NO:5), where X is any nucleotide. In other embodiments, a non-AAV ITR encapsidation element comprises a terminal resolution site. In some of these embodiments, a terminal resolution site has the nucleotide sequence GGTTGG. In other embodiments, a non-AAV ITR encapsidation element comprises both a Rep68/Rep78 binding site and a terminal resolution site. In some of these embodiments, a non-AAV ITR comprises the nucleotide sequence GGTTGG(X)nGCXCGCTCGCTCGCTX (SEQ ID NO:6), wherein X is any nucleotide and n is a number from 1 to about 100, preferably about 50, more preferably about 20, more preferably about 10.

A non-AAV ITR encapsidation element for use in the present invention promotes (or increases, or enhances) encapsidation of an operably linked heterologous gene into an AAV particle. Those skilled in the art can readily determine whether a given nucleotide sequence functions as an encapsidation element. Any of a variety of methods known to those skilled in the art can be employed for this determination, including, but not limited to, measuring the number of DRPs (i.e., encapsidated recombinant vectors), and subjecting the DRPs to hybridization analysis, as described in Example 2. A non-AAV ITR encapsidation element for use in the present invention promotes encapsidation of an operably linked heterologous gene such that at least about $10^2$, more preferably at least about $10^4$, more preferably at least about $10^6$, more preferably at least about 1 more preferably at least about $10^8$, more preferably at least about $10^9$, even more preferably at least about $10^{10}$ or more, DRP containing the heterologous gene per milliliter are generated when the vector is provided in a mammalian cell which synthesizes AAV rep and cap gene products, and to which mammalian cell is provided helper virus function(s).

Isolated Recombinant Polynucleotides Comprising a Heterologous Gene Operably Linked to a Non-AAV ITR Encapsidation Element Urcelay et al. ((1995) J. Virol. 69:2038–2046) describe a plasmid, pMAT50, which comprises a P1 element and a lacZ gene and an AAV ITR. No encapsidation function was attributed to this P1 element. The present invention provides an isolated recombinant polynucleotide (also referred to herein as an isolated recombinant vector) comprising a non-AAV ITR encapsidation element operably linked to a heterologous gene(s), wherein the encapsidation element promotes encapsidation of the operably linked heterologous gene into an AAV particle under conditions permissive for encapsidation, and wherein the isolated recombinant vector is not pMAT50. Conditions permissive for encapsidation are provided when the isolated recombinant polynucleotide is in a mammalian cell which synthesizes AAV rep and cap gene products, and which is provided with helper virus function. In these embodiments, the isolated recombinant polynucleotide is introduced into a mammalian cell which synthesizes AAV rep and cap gene products. When helper virus function is further provided, the isolated recombinant polynucleotide is encapsidated in AAV particles.

We have observed that placing an encapsidation element, as exemplified by a P1 sequence, near a heterologous gene, e.g., a cap gene, resulted in a efficient packaging of the heterologous gene in AAV particles. Indeed, as shown below, a P1 element placed at a distance of 5.2 kb from the DHFR sequence, for example, resulted in efficient packaging of the heterologous gene with production of approximately $10^{10}$ DRPs per milliliter. This compares favorably with encapsidation efficiencies reported for ITR-mediated packaging of AAV vector genomes. Although placing an encapsidation element further away from an AAV packaging gene (e.g. 5–10 kb or further) may result in somewhat lower levels of encapsidation, longer distances between an encapsidation element and an operably linked heterologous gene would still be expected to provide a degree of encapsidation sufficient for production of isolated recombinant polynucleotides encapsidated in AAV particles. Accordingly, in some embodiments, the non-AAV ITR encapsidation element is less than about 10 kb, more preferably less than about 5 kb, more preferably less than about 4 kb, more preferably less than about 3 kb, more preferably less than about 2 kb, more preferably less than about 1 kb, more preferably less than about 0.5 kb away from (i.e., in the direction of encapsidation from) the isolated recombinant polynucleotide comprising a heterologous gene to be packaged into an AAV particle.

In some embodiments, the isolated recombinant polynucleotide further comprises a selectable marker. Once this recombinant polynucleotide is introduced into a mammalian cell, the cell can be subjected to selection appropriate to the selectable marker. A variety of selectable markers suitable for use in mammalian cells, and the manner of selection, are known in the art, and need not be described in detail herein. Any such selectable marker is suitable for use in the isolated recombinant polynucleotides of the invention. Mammalian cells comprising an isolated recombinant polynucleotide containing a selectable marker, subjected to selection appropriate to the selectable marker can yield cells which comprise the recombinant polynucleotide stably integrated into the genome of the cell, as described in the Examples. When such a cell synthesizes AAV rep and cap gene products, and exhibits helper virus function, or is provided with helper virus function, the recombinant polynucleotide can be rescued and encapsidated into AAV particles.

In encapsidating copies of integrated operably linked heterologous gene(s) in response to helper virus infection, the P1 element appears to direct encapsidation unidirectionally. Without wishing to be bound by theory, it is believed that interaction of Rep with a Rep-binding motif may be followed by nicking between the two residues in a Terminal Resolution Site (TRS), as illustrated below. Subsequently, replication may initiate from the 3' hydroxyl end of the nick and proceed toward the Rep-binding motif. Accordingly, in some embodiments, a unidirectional encapsidation element (for example, P1) is oriented such that unidirectional replication proceeds from the encapsidation element toward the associated (i.e., operably linked) heterologous gene(s).

Alternatively, a heterologous gene(s) can be flanked by encapsidation elements that are oriented so that replication initiated at each element proceeds "inward" toward the heterologous gene(s).

It is understood that while the polynucleotides containing the encapsidation element(s) and the heterologous gene(s) may be integrated, they may also exist in an episomal state.

In some embodiments, the isolated recombinant polynucleotides of the invention have a size no greater than the upper size limit for packaging into an AAV particle. In some of these embodiments, isolated recombinant polynucleotides of the invention have a size greater than about 5 kb. In some of these embodiments, isolated recombinant polynucleotides of the invention have a size less than about 5 kb. In some of these embodiments, the size of the isolated recombinant polynucleotide is about 4.7 kb or less. Examples of recombinant polynucleotides sizes packageable into an AAV particle include, but are not limited to, those sizes exemplified in Dong et al., 1996, *Human Gene Ther.* 7:2101–2112.

Production of AAV Particles Comprising a Heterologous Gene

To generate recombinant AAV particles useful for such purposes as gene therapy, or introducing a transgene into a cell, a packaging cell, or a packaging cell line, which synthesizes AAV rep and cap gene products, is generally supplied with a recombinant vector comprising a heterologous gene operably linked to an encapsidation element other than an AAV ITR or a D-sequence of an AAV ITR, such that the recombinant vector enters the cell and is packaged into an AAV particle in the presence of helper virus function(s). The vector can be introduced into the packaging cell by any known means, including, but not limited to, electroporation and lipofection. The packaging cell provides AAV rep and cap functions, which can be encoded by polynucleotide sequences which are stably integrated into the genome, or which are maintained in the packaging cell episomally, or are produced by transiently transfecting the cell with a vector, such as a plasmid vector, which comprises sequences encoding AAV rep and cap gene products. Helper functions can be provided by infecting the packaging cell with helper virus before, during, or after providing the cell with the recombinant vector. Alternatively, a vector which comprises nucleotide sequences which encode helper virus function(s) can be provided to the cell before, during, or after providing the cell with the recombinant vector. In some embodiments, the recombinant vector is provided to the cell transiently. In other embodiments, the recombinant vector comprises a selectable marker and the packaging cell is selected on the basis of the selectable marker such that the recombinant vector is stably integrated into the genome of the packaging cell. In other embodiments, the recombinant vector can stably integrate into the genome of the packaging cell without the need for a selectable marker.

Heterologous Polynucleotides

The heterologous polynucleotide, if it is intended to be expressed, is generally operably linked to a promoter, either its own or a heterologous promoter. A large number of suitable promoters are known in the art, the choice of which depends on the desired level of expression of the target polynucleotide; whether one wants constitutive expression, inducible expression, cell-specific or tissue-specific expression, etc. The recombinant vector can also contain a positive selectable marker in order to allow for selection of cells that have been infected by the recombinant vector;

and/or a negative selectable marker (as a means of selecting against those same cells should that become necessary or desirable); see, e.g., S. D. Lupton, PCT/US91/08442 and PCT/US94/05601.

As an example, a recombinant vector can be constructed which comprises an encapsidation element operably linked to a polynucleotide that encodes a functional cystic fibrosis transmembrane conductance regulator polypeptide (CFTR) operably linked to a promoter. As is now known in the art, there are a variety of CFTR polypeptides that are capable of reconstituting CFTR activity in cells derived from cystic fibrosis patients. For example, Carter et al. have described truncated variants of CFTR genes that encode functional CFTR proteins (see, e.g., U.S. Pat. No. 5,866,696). See also, Rich et al. (1991, *Science* 253: 205–207) who have described a CFTR derivative missing amino acid residues 708–835, that was capable of transporting chloride and capable of correcting a naturally occurring CFTR defect, and Egan et al. (1993) who described another CFTR derivative (comprising about 25 amino acids from an unrelated protein followed by the sequence of native CFTR beginning at residue 119) that was also capable of restoring electrophysiological characteristics of normal CFTR. To take two additional examples, Arispe et al. (1992, *Proc. Natl. Acad. Sci. USA* 89: 1539–1543) showed that a CFTR fragment comprising residues 433–586 was sufficient to reconstitute a correct chloride channel in lipid bilayers; and Sheppard et al. (1994, *Cell* 76:1091–1098) showed that a CFTR polypeptide truncated at residue 836 to about half its length was still capable of building a regulated chloride channel. Thus, the native CFTR protein, and mutants and fragments thereof, all constitute CFTR polypeptides that are useful in the practice of this invention.

Other useful target polynucleotides can be used in this invention to generate recombinant vectors for a number of different applications. Such polynucleotides include, but are not limited to: (i) polynucleotides encoding proteins useful in other forms of gene therapy to relieve deficiencies caused by missing, defective or sub-optimal levels of a structural protein or enzyme; (ii) polynucleotides that are transcribed into anti-sense molecules; (iii) polynucleotides that are transcribed into decoys that bind transcription or translation factors; (iv) polynucleotides that encode cellular modulators such as cytokines; (v) polynucleotides that can make recipient cells susceptible to specific drugs, such as the herpes virus thymidine kinase gene; and (vi) polynucleotides for cancer therapy, such as the wild-type p53 tumor suppressor cDNA for replacement of the missing or damaged p53 gene associated with over 50% of human cancers, including those of the lung, breast, prostate and colon.

Mammalian Packaging Cells

The present invention provides mammalian packaging cells for producing stocks of a recombinant polynucleotide encapsidated in an AAV particle, wherein the recombinant polynucleotide comprises a heterologous gene operably linked to a non-AAV ITR encapsidation element which promotes encapsidation of the operably linked heterologous gene into the AAV particle.

For production of a recombinant polynucleotide encapsidated in an AAV particle, wherein the recombinant polynucleotide comprises a heterologous gene operably linked to a non-AAV ITR encapsidation element, and preferably to a non-AAV ITR D-sequence encapsidation element, a mammalian cell which synthesizes AAV rep and cap gene products, i.e., a packaging cell, is used. AAV rep and cap gene products can be encoded by stably integrated AAV rep and cap genes, or can be encoded by polynucleotides comprised in a vector which is introduced into the cell before, during, or after introduction of the recombinant vector. Further, stable cell lines can be generated which comprise the recombinant vector stably integrated into the genome of the cell.

Since the therapeutic specificity of the resulting recombinant vector is determined by the plasmid introduced, the same packaging cell line can be used for any of these applications. The plasmid comprising the specific target polynucleotide is introduced into the packaging cell for production of the AAV vector by any known method; including, but not limited to, electroporation.

A number of packaging cells comprising stably integrated AAV cap and/or rep genes are known in the art and can be used for packaging the recombinant vectors described herein. see, e.g., T. Flotte et al., WO 95/13365 (Targeted Genetics Corporation and Johns Hopkins University), and corresponding U.S. Pat. No. 5,658,776; J. Trempe et al., WO 95/13392 (Medical College of Ohio), and corresponding U.S. Pat. No. 5,837,484; and J. Allen, WO 96/17947 (Targeted Genetics Corporation).

Such packaging cells include, but are not limited to, packaging cells which comprise a stably integrated AAV cap gene operably linked to a promoter and a stably integrated AAV rep gene operably linked to a heterologous promoter, for example as described by Allen (International Patent Application No. PCT/US95/15892); packaging cells comprising an AAV rep gene, which may be operably linked to a heterologous promoter; packaging cells comprising an AAV cap gene operably linked to a promoter. When packaging cells comprising stably integrated rep and cap genes are used, the recombinant vector comprising a heterologous gene operably linked to an encapsidation element is introduced into the cell, and, in the presence of helper virus function, the recombinant vector is packaged into AAV particles. When packaging cells comprising stably integrated AAV rep or AAV cap genes are used, the missing in trans product is supplied, typically on a plasmid vector which is introduced before, simultaneously with, or after, introduction of the recombinant vector.

In other embodiments, the packaging cells are provided with both AAV rep and AAV cap gene products by introducing into the cell a vector comprising coding sequences for AAV rep and cap gene products before, simultaneously with, or after, introduction of the recombinant vector comprising a heterologous gene operably linked to an encapsidation element. Plasmid-encoded AAV rep and/or cap genes can optionally be maintained episomally.

In other embodiments, also illustrated in the Examples below, the recombinant vector is itself stably integrated into a packaging cell line. Such stable, vector-containing packaging lines can also optionally contain stable chromosomal or episomal copies of AAV cap and/or rep genes. Cell lines such as those described above can be grown and stored until ready for use. To induce production of recombinant vector packaged into AAV particles in cells that contain Rep and Cap proteins, the user simply infects the cells with helper virus, or provides helper functions on a plasmid introduced by any known method, and cultures the cells under conditions suitable for replication and packaging of AAV (as described below).

Helper Virus Function

Helper virus can be introduced before, during or after introduction of the recombinant vector. For instance, the plasmid can be co-infected into the culture along with the helper virus. The cells are then cultured for a suitable period, typically 2–5 days, in conditions suitable for replication and packaging as known in the art (see references above and examples below). Lysates are prepared, and the recombinant AAV vector particles are purified by techniques known in the art. Alternatively, helper virus functions are provided to the cell on recombinant vectors, such as plasmids.

Purification of Recombinant Vectors

Recombinant vectors encapsidated in AAV particles prepared using the methods and compositions of the present invention can be purified according to techniques known in the art, see, e.g., the various AAV references cited above. Alternatively, improved purification techniques can be employed, such as those described by Atkinson et al. in International Patent Application No. PCT/US98/18600.

Introduction of Heterologous Genes into a Cell Using Encapsidated Recombinant Vectors of the Invention The recombinant vectors encapsidated into AAV particles can be used to deliver polynucleotides to target cells either in vitro, in vivo, or ex vivo, as described in the references cited herein and in the art. For delivery in vivo, the recombinant vectors encapsidated in AAV particles will typically be contained in a physiological suitable buffered solution that can optionally comprise one or more components that promote sterility, stability and/or activity. Any means convenient for introducing the vector preparation to a desired location within the body can be employed, including, for example, by intravenous or localized injection, by infusion from a catheter or by aerosol delivery.

The examples presented below are provided as a further guide to a practitioner of ordinary skill in the art, and are not meant to be limiting in any way.

EXAMPLES

Example 1

Construction of Recombinant Vectors Comprising a Non-AAV ITR Encapsidation Element Operably Linked to a Heterologous Gene, and Cells Comprising the Vectors.

1. Construction of a Recombinant Vector Employing P1 as an Exemplary Encapsidation Element An exemplary P1 sequence we used as the source of encapsidation element comprises nucleotides 354–468 of the AAV S1 locus (Kelman et al (1994) Curr. Opin. Genet. Dev. 4:185–195; Weitzman et al (1994) Proc. Natl. Acad. Sci. 91:5808–5817). Shown below is the nucleotide sequence of a P1 encapsidation element (SEQ ID NOs. 1 and 2), including a presumed terminal resolution site (TRS) at nucleotides 19–24 of SEQ ID NO: 1 (i.e., nucleotides 372–377 of the AAV S1 locus), and a presumed Rep binding motif (RB Motif, also known as a Rep-binding site or RBS), at nucleotides 33–48 of SEQ ID NO:1 (i.e., nucleotides 386–401 of the AAV S1 locus). Also indicated (by the downward-pointing arrow) is the presumed Rep cleavage site located between the thymidines of the TRS.

cap encoding sequences transcriptionally linked to the native p5, p19 and p40 promoters and followed by the AAV2 polyadenylation signal, was constructed as follows. Briefly, a fragment from pAV2 comprising nucleotides 193 to 379 (Srivastiva et al. (1983) J. Virol. 45:555–564) was obtained by PCR amplification. The design of the PCR primers resulted in addition of a BglII site at the 5' end of the amplified fragment and encompassed the PpuMI site (at AAV-2 nucleotide 350) close to the 3' end. The PCR-amplified DNA was digested with BglII and PpuMI to generate a restriction fragment comprising AAV-2 nucleotides 193–350. A restriction fragment comprising nucleotides 351–4498 of pAV2 was isolated from pAV2 by digestion with PpuMI and SnaBI. These two fragments (representing nucleotides 193–4498 of pAV2) were ligated into a tgLS(+)HyTK retroviral vector (S. D. Lupton et al., Molecular and Cellular Biology, 11: 3374–3378, 1991) in a four-way ligation that also included a StuI-BstEII fragment of tgLS(+)HyTK and a BstEI-StuI fragment of tgLS(+)HyTK to which a BglII linker had been attached at the StuI end. This ligation generated tgLS(+)HyTK-repcap. Subsequently, a BglII-ClaI fragment from tgLS(+)HyTK-repcap, including AAV rep and cap genes transcriptionally linked to the native p5, p19 and p40 promoters and followed by the AAV2 polyadenylation signal, was isolated and cloned into the BamHI and ClaI sites of pSP72 (Promega).

3. Construction of p5repcapDHFR

Expression plasmid p5repcapDHFR was constructed for the purpose of producing an integrated packaging line including the construct p5repcap (Example 1, section 2) and a modified dihydrofolate reductase gene (DHFR) as a selectable marker. Specifically, p5repcap (Example 1, section 2) was linearized at a PvuII site located just upstream of the rep gene, and blunt-end ligated to a 1.8 kb fragment of pFR400 (Simonsen et al. (1983) Proc. Natl. Acad. Sci. USA 80:2495–2499). This pFR400 fragment comprises a modified DHFR gene, with a reduced affinity for methotrexate (Mtx), transcriptionally linked to the SV40 early promoter and followed by the polyadenylation site from the Hepatitis virus (HBV) surface antigen gene. The pFR400 fragment was prepared by first digesting with SalI, followed by a four base pair fill-in (to generate a blunt end) and subsequent PvuII digestion and gel purification. The resulting construct, p5repcapDHFR (FIG. 4), contains a DHFR gene whose transcription is regulated by an upstream SV40 early promoter and a downstream Hepatitis Virus polyadenylation site. Immediately downstream of this DHFR transcriptional cassette lie the AAV rep and cap genes, followed by an AAV polyadenylation site.

4. Addition of P1 to a Repcap-Containing Plasmid: Construction of P1RCD

A P1 element (Example 1, section 1) was then incorporated into expression plasmid p5repcapDHFR (Example 1,

```
                     TRS
SEQ ID NO:1           ↓
5' CGGGCGGGTGGTGGCGGCGGTTGGGGCTCGCGCTCGCTCGCTCGCTGGGCGGGCGGGCGGT 3'
   ||||||||||||||||||||||||||||||||||||||||||||||||||||||||||||
3' GCCCGCCCACCACCGCCGCCAACCCCGAGCCGCGAGCGAGCGAGCGACCCGCCCGCCCGCCA 5'
SEQ ID NO:2                          RB Motif
```

2. Construction of p5repcap

Figure 5:
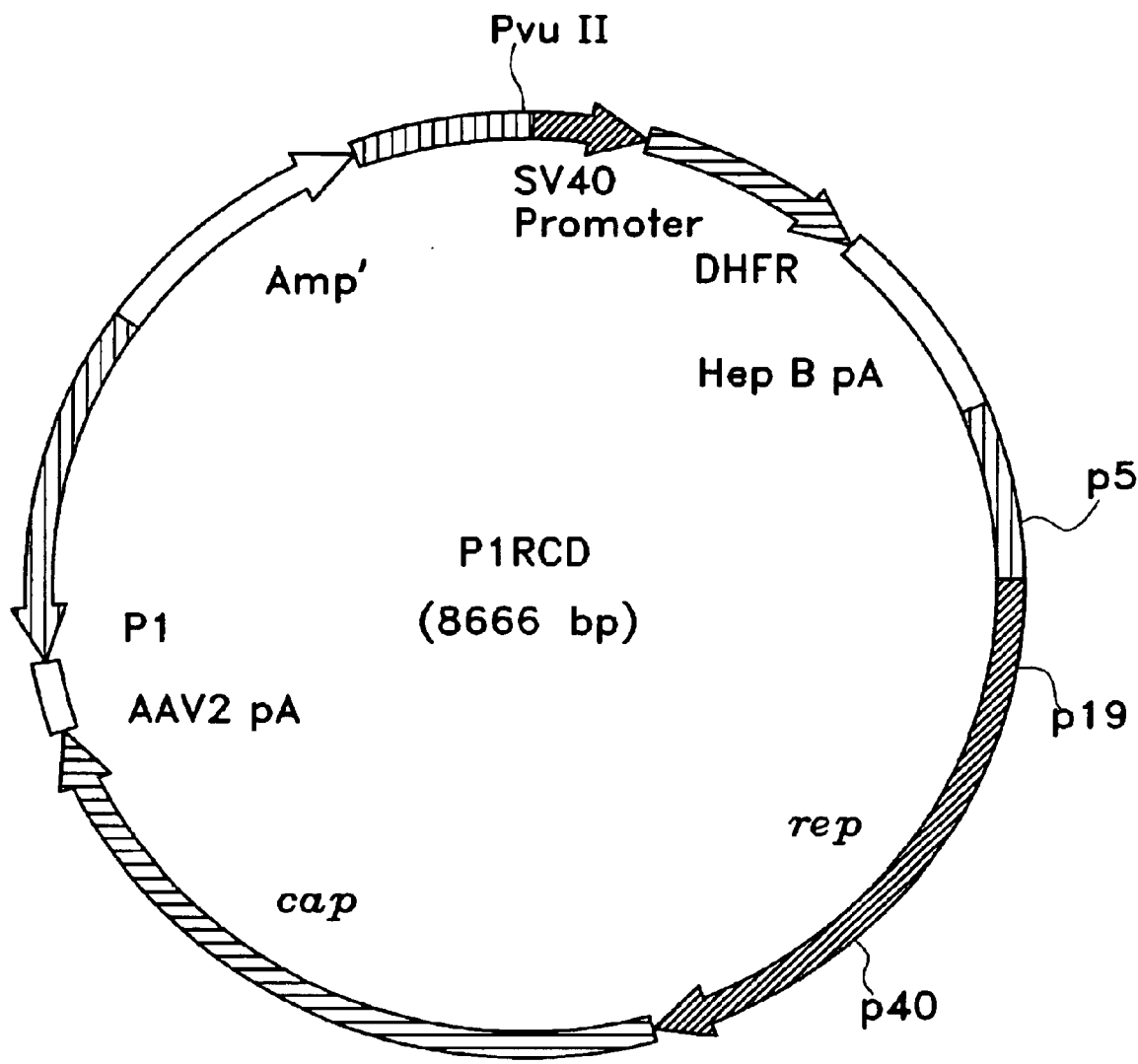
FIG. 5 shows a map of the P1RCD plasmid.

We linked a P1 element (as described above) to AAV rep and cap genes that remained operably linked to their native AAV promoters. As a first step in that process, an AAV packaging cassette, p5repcap, comprising the AAV rep and section 3). In the construction of the plasmid, "P1RCD", containing this packaging cassette, the P1 element was inserted downstream of the AAV polyadenylation signal in p5repcapDHFR in an orientation such that replication initiating from the P1 element proceeds first into the cap gene and then into the rep gene (i.e., replication initiates at the 3'
—OH of the TRS on the anti-sense strand and proceeds in
a 5'-to-3' direction towards the cap gene). To facilitate
insertion of the P1 element into p5repcapDHFR, a pair of
oligonucleotides was synthesized which include the P1
sequence flanked by ends compatible with a BglII restriction
site (see sequences below, SEQ ID NOs. 3 and 4). The pair
was annealed, then ligated to p5repcapDHFR previously
linearized at a BglII site located just downstream of the AAV
polyadenylation site (Example 1, section 3, nucleotide
6217). A clone named P1RCD was selected, containing a P1
insert in an orientation such that replication initiated at P1
proceeds in the direction of the cap and rep genes (FIG. 5).
This vector contains no AAV ITR sequences.

containing 10% dialyzed fetal bovine serum, 1% penicillin,
streptomycin, and L-glutamine plus 500 nM methotrexate.
Wells were visually inspected for cell growth and the
presence of single colonies. Clones were expanded from
96-well plates with 15 or fewer positive wells per plate and
from wells containing single colonies. Cells were maintained under selection of 500 nM methotrexate in DMEM
containing 10% dialyzed serum until individual clones were
frozen. Clones were screened for the presence of the P1
RCD construct. Positive clonal cell lines were frozen and
stored in liquid nitrogen. The C29 clonal cell line containing
the P1RCD construct was chosen for subsequent experiments.

```
SEQ ID NO:3                    RB Motif
5' GATCACTAGTACCGCCCGCCCGCCCAGCGAGCGAGCGAGCGCCGAGCCCCAACCGCCGCCACCACCCGCCCGA 3'
           ||||||||||||||||||||||||||||||||||||||||||||||||||||||||||||||||
3'     TGATCATGGCGGGCGGGCGGGTCGCTCGCTCGCTCGCGGCTCGGGGTTGGCGGCGGTGGTGGGCGGGCTCTAGA 5'
SEQ ID NO:4                                                     TRS
```

5. Construction of rAAV Vector ACAPSN

The plasmid ACAPSN was constructed according to
Lynch et al. (1997) Circ. Res. 80: 497–505 and PCT
Publication WO 97/32990, as follows. The ITR sequences
and plasmid backbone were derived from AAV-CFTR.
Afione et al. (1996) J. Virol. 70:3235–3241. Briefly, the
AAV-CFTR vector was digested with XhoI and SnaBI and
the ITRs and plasmid backbone were gel isolated. An XhoI
to SnaBI fragment containing a portion of the CMV promoter (nucleotides −671 to −464) [See, e.g., Boshart, et al.,
Cell, 41: 521–530 (1985)] was gel isolated and ligated to the
ITR plasmid backbone fragment derived from AAV-CFTR
to generate "pAAV-CMV (SnaBI)." Next, an SpeI to SnaBI
fragment containing the synthetic polyadenylation signal
was inserted into SpeI/SnaBI digested pAAV-CMV (SnaB 1)
to generate "pAAV-CMV (SpeI)-spA." The pAAV-CMV
(SpeI)-spA vector contains nucleotides −671 to −584 of the
CMV promoter. Next, the human placental alkaline phosphatase cDNA sequence linked to the Simian virus 40
promoter driving the E. coli neomycin gene was isolated
from LAPSN [See, e.g., Clowes et al., 1994, J. Clin. Invest.
93:644–651] as an SpeI to NheI fragment and inserted into
pAAV-CMV (SpeI)-spA (which had been linearized with
SpeI) to create "pAAV-APSN." An SpeI to NheI fragment
containing CMV promoter nucleotides −585 to +71 was
inserted into SpeI-linearized pAAV-APSN to generate vector "ACAPSN."

6. Production of Packaging Cell Lines Containing P1RCD

Polyclonal cell lines with an integrated AAV packaging
cassette containing the P1 element (P1RCD) were produced
by electroporation of HeLa cells. Specifically, $4 \times 10^6$ HeLa
cells were electroporated with 12 μg DNA (P1RCD) that had
been linearized with PvuII restriction endonuclease, which
cleaves just upstream of the SV40 promoter-DHFR gene
cassette. The cells were electroporated in serum free DMEM
using a BioRad Gene Pulser at 0.25 Volts and 960 μF. After
electroporation, cells were resuspended in Dulbecco's
Modified Eagles medium, 10% fetal bovine serum, with 1%
penicillin and streptomycin (DMEM complete) and allowed
to recover at 37° C. in a humidified atmosphere of 10% $CO_2$.
After 24 hours, cells were subjected to selection in complete
medium containing 500 nM methotrexate.

7. Production of P1 RCD Clonal Cell Lines

P1RCD polyclonal cells were plated in 96-well plates at
a density of 1, 0.3, and 0.1 cell per well in DMEM 8. Production of Producer Cell Lines P1/ACAPSN and P1/ALinBg Producer cell line P1/ACAPSN was generated by electroporating P1RCD C29 packaging cells in an analogous
manner as the P1RCD packaging line above. Specifically,
$4 \times 10^6$ P1RCD C29 cells were electroporated with 10 μg of
tgACAPSN DNA that had been linearized with Xmn I
endonuclease. Electroporation conditions are described in
Example 1, section 6. After electroporation, the cells were
resuspended in DMEM complete and allowed to recover at
37° C. for 24 hours. Cells were then subjected to selection
in complete media containing 1 mg/ml G418. Clones of
P1/ACAPSN were selected and expanded in the manner
described above (Example 1, section 7) using 1 mg/ml G418
as selection media. The P1/ACAPSN C 19 cell line was
chosen for subsequent experiments. Clones were screened
for the ability to produce ACAPSN virions according to
Example 2.

P1/ALinBg clones were produced in an analogous manner
by electroporating P1RCD C29 cells with ALinBg DNA.

Example 2
P1 Element Promotes Encapsidation of Operably Linked Gene into AAV Particles.

1. Production of Virions

C29 cells (Example 1, section 7) were seeded at a density
of $5 \times 10^6$ cells in a T225 $cm^2$ flask one day prior to infection
with adenovirus (Ad). Four replicate flasks were seeded.
Twenty-four hours later, one flask of cells was treated with
trypsin and the number of cells counted. The remaining three
flasks of cells were infected with Ad at a multiplicity of
infection of 10. Seventy-two hours later cells were collected
by centrifugation and resuspended to a concentration of
$5 \times 10^6$ cells/mL in 50 mM TRIS, pH 8.0, 5 mM $MgCl_2$, 1
mM EDTA, 5% glycerol (TMEG). Cells were subjected to
repeated freeze/thaw (−70° C./37° C.) cycles and sonication
(4×15 sec bursts). After confirmation that greater than 95%
of the cells were lysed, cell debris was removed by low
speed centrifugation. The resulting cleared lysates were
examined for the presence of encapsidated P1 RCD DNA
sequences.

2. DRP Slot-Blot Analysis

Encapsidated DNA sequences were examined by DNA
hybridization following DNase treatment of cleared lysates.
A number of radiolabeled probes were generated which
spanned the P1RCD construct: cap; repcap; DHFR#1
(DHFR gene and hepatitis polyadenylation signal); and
DHFR #2 (DHFR coding sequences only). The number of DNase Resistant Particles (DRP) was quantitated by comparison to a standard curve included on each slot-blot. P1RCD plasmid DNA was used to generate standards.

DNase resistant, i.e. encapsidated, DNA sequences were detected in cleared lysates generated from C29 cells with each of the P1 RCD probes, as shown in Table 1, below. In general, the number of DNase Resistant Particles was on the order of $1 \times 10^{10}$/mL. This level of encapsidation is comparable to that typically seen with ITR-mediated packaging of AAV vector genomes.

TABLE 1

| Probe | DRP/mL |
|---|---|
| rep-cap | $1 \times 10^{10}$ |
| cap | $1 \times 10^{10}$ |
| DHFR #1 | $1.3 \times 10^{10}$ |
| DHFR #2 | $1.3 \times 10^{10}$ |

Example 3

Characterization of the P1 Encapsidation Element.

1. The P1 Encapsidation Element is Included in the Encapsidated DNA

DNase resistant, i.e. encapsidated, DNA sequences were detected in cleared lysates generated from C29 cells using a P1 probe. Oligonucleotides comprising the P1 element were synthesized, annealed and end-labeled. Similar numbers of virions were detected with the 1 probe ($2 \times 10^{10}$ DRP/mL) as previously detected with the rep-cap, cap and DHFR probes. This indicates that the P1 encapsidation element is included in the encapsidated DNA sequences.

2. P1 Encapsidation Element Promotes Encapsidation of Sense and Anti-Sense DNA Strands at an Equal Ratio.

Duplicate slot-blots of DNase-treated C29 cleared lysate were individually hybridized with oligonucleotide probes representing the 5' to 3' and 3' to 5' sequences of the P1 element. Titers of DRPs observed with the sense and anti-sense P1 probes were $2.6 \times 10^{10}$ and $1.3 \times 10^{10}$ DRP/mL, respectively. It appears that the P1 encapsidation element directs encapsidation of DNA strands of either polarity at equal frequency.

3. P1 Encapsidation Element Promotes Packaging in a Vector Producer Cell Line in the Presence of ITR Sequences Slot-blots of DNase treated P1/ACAPSN C19 cleared lysate were hybridized with the cap, DHFR#1 and DHFR#2 probes described in Example 2, section 2, above. The number of ACAPSN vector particles present was also determined using a CMV probe. The results are shown in Table 2. "NA" indicates "not applicable"

TABLE 2

| Probe | DRP/mL (P1 packaging) | DRP/mL (ITR Packaging) |
|---|---|---|
| cap | $3 \times 10^9$ | NA |
| DHFR #1 | $2.7 \times 10^9$ | NA |
| DHFR #2 | $2.3 \times 10^9$ | NA |
| CMV | NA | $1.3 \times 10^{11}$ |

Both ITR- and P1-promoted encapsidation of DNA sequences were observed in P1/ACAPSN C19 cleared lysate. The titer of particles containing recombinant polynucleotides operably linked to P1 (i.e., P1-directed encapsidation) was one-half log lower than previously observed in the C29 clonal cell line, which lacks an ITR-flanked ACAPSN vector cassette. These data demonstrate that the P1 element can function as a packaging signal even in the presence of a bona fida AAV ITR packaging signal.

4. Encapsidated DNA Sequences in Purified Recombinant Vector Preparations from HeLa Cells Containing a P1 Element Large-scale vector preparations were manufactured from the P1/ACAPSN C19 cell line and purified by CsCl ultracentrifugation and ion-exchange chromatography. Two independent lots of vector were manufactured. In addition to the ACAPSN vector particles, the purified preparations contained encapsidated DNase resistant particles which contained recombinant polynucleotides operably linked to P1.

Another P1 producer cell line was independently generated from an AAV vector carrying the β-galactosidase reporter gene (ALinBg). Vector preparations manufactured from the P1/AlinBg producer cell line also contained DNAse resistant particles containing recombinant polynucleotides operably linked to P1, in addition to ALinBg vector particles.

Southern Analysis

Figure 6:
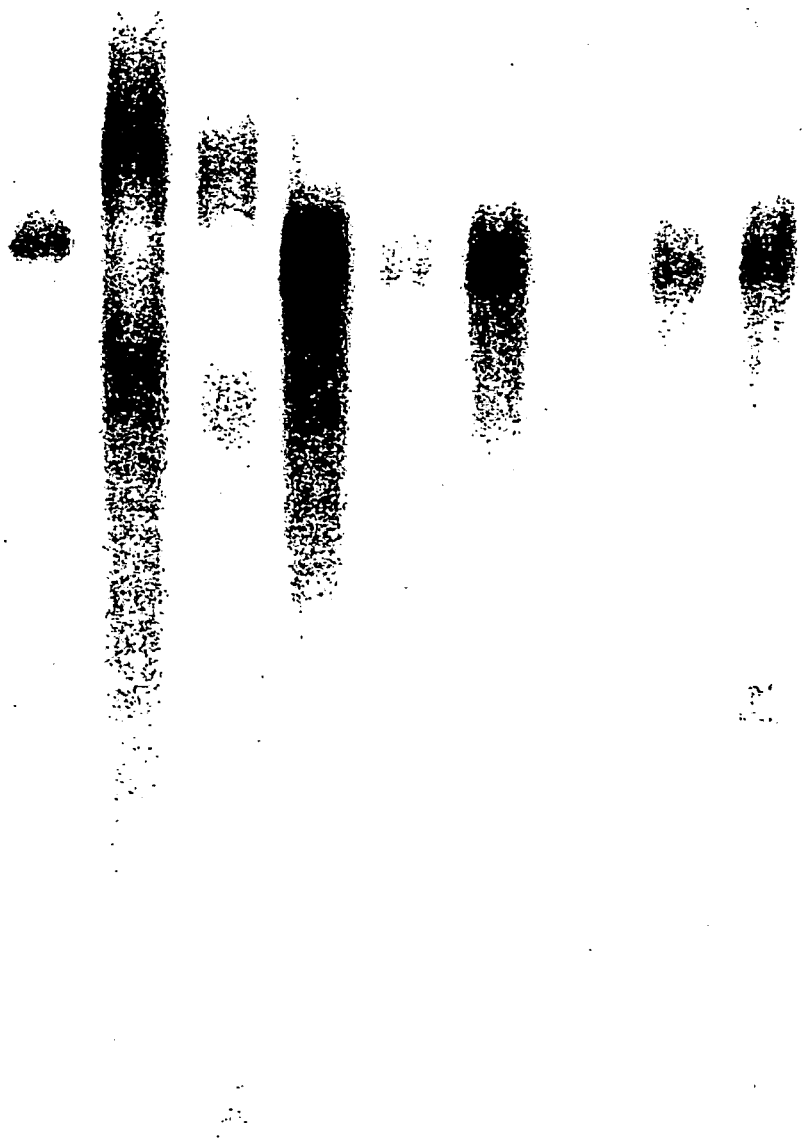
FIG. 6 depicts an autoradiograph showing results of experiments performed to determine the sizes of recombinant vectors encapsidated in AAV particles, as described in Example 3. Numbers on the left-hand side are sizes, in kilobases, of DNA. Lane 1, 4.8 kb Bgl II to Nae I fragment from plasmid P1RCD; lane 2, $10^8$ DRP of lysate from C29 cells; lane 3, $10^8$ DRP of lysate from C29 cells treated with DNase; lane 4, $10^9$ DRP of lot 1 purified virions from P1/ACAPSN; lane 5, $10^8$ DRP of lot 1 purified virions from P1/ACAPSN; lane 6, $10^9$ DRP of lot 2 purified virions from P1/ACAPSN; lane 7, $10^8$ DRP of lot 2 purified virions from P1/ACAPSN; lane 8, $10^8$ DRP of lot 1 purified virions from P1/ALinBg; lane 9, $10^8$ DRP of lot 2 purified virions from P1/ALinBg.

The P1-encapsidated DNA was examined by Southern blot analysis. Purified virions from the P1/ACAPSN and P1/AlinBg cell lines were lysed and the encapsidated DNA fractionated by electrophoresis in alkaline gels. A predominant band of approximately 4.7 kb in size was observed in all vector lots when hybridized with a rep-cap probe, as shown in FIG. 6. This suggests that the predominant DNA species packaged using the P1 packaging signal are similar in size to the wild-type AAV genome length, i.e the normal AAV packaging capacity.

Thus, using two different AAV vectors and two producer cell lines independently derived from the C29 packaging cell line, we have observed P1 promoted encapsidation of cis linked sequences. Furthermore, P1-promoted packaging occurred in the presence of ITR-mediated encapsidation of recombinant AAV vectors. The P1 packaged sequences were co-purified with rAAV virions by CsCl isopycnic ultracentrifugation and survived treatment with DNase and heating to 54° C. for 10 minutes. This indicates that P1 promotes encapsidation into AAV particles that are robust and can be purified by methods used for recombinant AAV vectors.

Example 4

Construction and Encapsidation of a Recombinant Polynucleotide Comprising a P1 Element Operably Linked to Coding Sequences for CFTR.

The region comprising AAV rep and cap genes is excised by BglII restriction endonuclease digestion from P1RCD and the fragment including P1 element and DHFR gene is isolated. A DNA fragment encoding CFTR and having compatible restriction endonuclease overhangs with the P1-containing fragment is isolated. The P1-containing fragment is ligated to the DNA fragment encoding CFTR, to produce a recombinant polynucleotide in which a P1 element is operably linked to sequences encoding CFTR.

This recombinant polynucleotide is introduced into a mammalian cell line producing AAV rep and cap gene products, and subsequently the cell line is infected with Ad helper virus.

Cells are lysed and DRPs are measured in the cleared lysates, as described above, then analyzed by slot blot hybridization with probes which hybridize to the P1 element and to CFTR-coding regions.

Although the foregoing invention has been described in some detail by way of illustration and example for purposes of clarity of understanding, it will be apparent to those skilled in the art that certain changes and modifications will be practiced. Therefore, the description and examples should not be construed as limiting the scope

What is claimed is:

1. A method for producing a recombinant polynucleotide encapsidated in an adeno-associated virus (AAV) particle, comprising culturing a mammalian cell which produces AAV rep and cap gene products under conditions that are permissive for encapsidation of a recombinant polynucleotide into an AAV particle, wherein said mammalian cell contains the recombinant polynucleotide which comprises a heterologous gene operably linked to an encapsidation element which promotes encapsidation of said heterologous gene into an AAV particle, wherein said encapsidation element is other than an AAV inverted terminal repeat (ITR) or its sequence, and wherein said encapsidation element comprises the nucleotide sequence GGTTGG(X)nGCXCGCTCGCTCGCTX (SEQ ID NO:7), wherein X is any nucleotide and n is an integer from 1 to about 20; and wherein the heterologous gene is a foreign gene to AAV;

whereby the recombinant polynucleotide encapsidated in the AAV particle is produced.

2. The method of claim 1, wherein said encapsidation element comprises a nucleotide sequence which has at least about 47% nucleotide sequence identity with SEQ ID NO: 1.

3. The method of claim 1, wherein said encapsidation element comprises at least about 35 contiguous nucleotides of the nucleotide sequence depicted in SEQ ID NO: 1.

4. The method of claim 1, wherein said encapsidation element comprises a nucleotide sequence having the sequence of nucleotides 19 to 48 counted from 5' end of SEQ ID NO:1.

5. The method of claim 1, wherein said encapsidation element comprises the nucleotide sequence depicted in SEQ ID NO: 1.

6. The method of claim 1, wherein the encapsidation activity of said encapsidation element is activated by helper function.

7. The method of claim 6, wherein said helper function is provided by an adenovirus.

8. The method of claim 1, wherein said AAV rep and cap gene products produced by said mammalian cell are encoded by AAV rep and cap genes which are stably integrated into the genome of said cell.

9. The method of claim 1, wherein said AAV rep and cap gene products are encoded by an extrachromosomal polynucleotide.

10. A method for generating a packaging cell capable of producing stocks of a recombinant polynucleotide comprising a heterologous gene encapsidated in an adeno-associated virus (AAV) particle, comprising transfecting mammalian cells which produce AAV rep and cap gene products with a recombinant polynucleotide, wherein said recombinant polynucleotide comprises a heterologous gene operably linked to an encapsidation element other than an AAV inverted terminal repeat (ITR) or an AAV ITR D sequence, wherein said encapsidation element promotes encapsidation of said heterologous gene into an AAV particle, and wherein said encapsidation element comprises the nucleotide sequence GGTTGG(X)nGCXCGCTCGCTCGCTX (SEQ ID NO:7), wherein X is any nucleotide and n is an integer from 1 to about 20; wherein the heterologous gene is a foreign gene to AAV.

11. The method of claim 10, wherein said AAV rep and cap gene products produced by said mammalian cell are encoded by AAV rep and cap genes stably integrated into the genome of the cell.

12. The method of claim 10, wherein said AAV rep and cap gene products are encoded by an extrachromosomal polynucleotide.

13. The method of claim 10, wherein said recombinant polynucleotide further comprises a selectable marker.

14. The method of claim 10, wherein said recombinant polynucleotide integrates into the genome of the cell.

15. The method of claim 10, wherein said encapsidation element comprises a nucleotide sequence which has at least about 47% nucleotide sequence identity with SEQ ID NO:1.

16. The method of claim 10, wherein said encapsidation element comprises a nucleotide sequence having the sequence of nucleotides 19 to 48 counted from 5' end of SEQ ID NO:1.

17. The method of claim 10, wherein said encapsidation element comprises at least about 35 contiguous nucleotides of the nucleotide sequence depicted in SEQ ID NO: 1.

18. The method of claim 10, wherein said encapsidation element comprises the nucleotide sequence depicted in SEQ ID NO: 1.

* * * * *

SEQUENCE LISTING

```
<160> NUMBER OF SEQ ID NOS: 16

<210> SEQ ID NO 1
<211> LENGTH: 62
<212> TYPE: DNA
<213> ORGANISM: Artificial Sequence
<220> FEATURE:
<223> OTHER INFORMATION: P1 Encapsidation Element

<400> SEQUENCE: 1
cgggcgggtg gtggcggcgg ttggggctcg gcgctcgctc gctcgctggg cgggcgggcg      60
gt                                                                    62

<210> SEQ ID NO 2
<211> LENGTH: 62
<212> TYPE: DNA
<213> ORGANISM: Artificial Sequence
<220> FEATURE:
<223> OTHER INFORMATION: P1 Encapsidation Element

<400> SEQUENCE: 2
accgcccgcc cgcccagcga gcgagcgagc gccgagcccc aaccgccgcc accaccgcc       60 cg                                                                    62

<210> SEQ ID NO 3
<211> LENGTH: 73
<212> TYPE: DNA
<213> ORGANISM: Artificial Sequence
<220> FEATURE:
<223> OTHER INFORMATION: P1 Oligonucleotide

<400> SEQUENCE: 3
gatcactagt accgcccgcc cgcccagcga gcgagcgagc gccgagcccc aaccgccgcc      60 accaccgcc cga                                                         73

<210> SEQ ID NO 4
<211> LENGTH: 74
<212> TYPE: DNA
<213> ORGANISM: Artificial Sequence
<220> FEATURE:
<223> OTHER INFORMATION: P1 Oligonucleotide

<400> SEQUENCE: 4
agatctcggg cgggtggtgg cggcggttgg ggctcggcgc tcgctcgctc gctgggcggg      60
cgggcggtac tagt                                                       74

<210> SEQ ID NO 5
<211> LENGTH: 16
<212> TYPE: DNA
<213> ORGANISM: Artificial Sequence
<220> FEATURE:
<223> OTHER INFORMATION: A non-AAV ITR encapsidation element
<220> FEATURE:
<221> NAME/KEY: misc_feature
<222> LOCATION: 3, 16
<223> OTHER INFORMATION: n = A, T, C, or G

<400> SEQUENCE: 5
gcncgctcgc tcgctn                                                     16

<210> SEQ ID NO 6
<211> LENGTH: 122
```

```
<212> TYPE: DNA
<213> ORGANISM: Artificial Sequence
<220> FEATURE:
<223> OTHER INFORMATION: A non-AAV ITR encapsidation element
<220> FEATURE:
<221> NAME/KEY: misc_feature
<222> LOCATION: (1)...(122)
<223> OTHER INFORMATION: All n's can or cannot be present
<220> FEATURE:
<221> NAME/KEY: misc_feature
<222> LOCATION: (1)...(122)
<223> OTHER INFORMATION: n = A, T, C, or G

<400> SEQUENCE: 6
ggttggnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnngcnc gctcgctcgc     120 tn                                                                    122

<210> SEQ ID NO 7
<211> LENGTH: 42
<212> TYPE: DNA
<213> ORGANISM: Artificial Sequence
<220> FEATURE:
<223> OTHER INFORMATION: A non-AAV ITR encapsidation element
<220> FEATURE:
<221> NAME/KEY: misc_feature
<222> LOCATION: (1)...(42)
<223> OTHER INFORMATION: All n's can or cannot be present
<220> FEATURE:
<221> NAME/KEY: misc_feature
<222> LOCATION: (1)...(42)
<223> OTHER INFORMATION: n = A, T, C, or G

<400> SEQUENCE: 7
ggttggnnnn nnnnnnnnnn nnnnnngcnc gctcgctcgc tn                         42

<210> SEQ ID NO 8
<211> LENGTH: 114
<212> TYPE: DNA
<213> ORGANISM: Artificial Sequence
<220> FEATURE:
<223> OTHER INFORMATION: P1 base pair smaI fragment

<400> SEQUENCE: 8
cccggggcgg gcgggcgggc gggtggtggc ggcggttggg gctcggcgct cgctcgctcg      60
ctgggcgggc gggcggtgcg atgtccggag aggatggccg gcggctggcc cggg           114

<210> SEQ ID NO 9
<211> LENGTH: 32
<212> TYPE: DNA
<213> ORGANISM: Artificial Sequence
<220> FEATURE:
<223> OTHER INFORMATION: Subfragment of the P1 base pair fragment

<400> SEQUENCE: 9
cgggcgggtg gtggcggcgg ttggggctcg gc                                    32

<210> SEQ ID NO 10
<211> LENGTH: 30
<212> TYPE: DNA
<213> ORGANISM: Artificial Sequence
<220> FEATURE:
<223> OTHER INFORMATION: Subfragment of the P1 base pair fragment

<400> SEQUENCE: 10
gctcgctcgc tcgctgggcg ggcgggcggt                                       30
```

<210> SEQ ID NO 11
<211> LENGTH: 67
<212> TYPE: DNA
<213> ORGANISM: Artificial Sequence
<220> FEATURE:
<223> OTHER INFORMATION: AAV2 ITR

<400> SEQUENCE: 11
aggaacccct agtgatggag ttggccactc cctctctgcg cgctcgctcg ctcactgagg    60
ccgcccc                                                              67

<210> SEQ ID NO 12
<211> LENGTH: 59
<212> TYPE: DNA
<213> ORGANISM: Artificial Sequence
<220> FEATURE:
<223> OTHER INFORMATION: AAV1 ITR

<400> SEQUENCE: 12
ttacccctag tgatggagtt gcccactccc tctctgcgcg ctcgctcgct cggtggggc     59

<210> SEQ ID NO 13
<211> LENGTH: 62
<212> TYPE: DNA
<213> ORGANISM: Artificial Sequence
<220> FEATURE:
<223> OTHER INFORMATION: AAV3 ITR

<400> SEQUENCE: 13 gccataccte tagtgatgga gttggccact ccctctatgc gcactcgctc gctcggtggg    60
gc                                                                   62

<210> SEQ ID NO 14
<211> LENGTH: 62
<212> TYPE: DNA
<213> ORGANISM: Artificial Sequence
<220> FEATURE:
<223> OTHER INFORMATION: AAV4 ITR

<400> SEQUENCE: 14
gggcaaacct agatgatgga gttggccact ccctctatgc gcgctcgctc actcactcgg    60
cc                                                                   62

<210> SEQ ID NO 15
<211> LENGTH: 76
<212> TYPE: DNA
<213> ORGANISM: Artificial Sequence
<220> FEATURE:
<223> OTHER INFORMATION: AAV5 ITR

<400> SEQUENCE: 15
acaaaacctc cttgcttgag agtgtggcac tctcccccct gtcgcgttcg ctcgctcgct    60
ggctcgtttg gggggg                                                    76

<210> SEQ ID NO 16
<211> LENGTH: 60
<212> TYPE: DNA
<213> ORGANISM: Artificial Sequence

```
-continued

<220> FEATURE:
<223> OTHER INFORMATION: AAV6 ITR

<400> SEQUENCE: 16
ttacccctag tgatggagtt gcccactccc tctctgcgcg ctcgctcgct cactgaggcc       60
```